United States Patent
Goldstein et al.

(10) Patent No.: US 8,998,031 B2
(45) Date of Patent: Apr. 7, 2015

(54) WASTE CONTAINER ASSEMBLY

(75) Inventors: Daniel E. Goldstein, Mundelein, IL (US); Kevin A. Pollack, Chicago, IL (US); John C. Japuntich, Harvard, IL (US); Scott I. Biba, Highland, WI (US); Mark S. Dirr, Kenosha, WI (US)

(73) Assignee: Stericycle, Inc., Northbrook, IL (US)

( * ) Notice: Subject to any disclaimer, the term of this patent is extended or adjusted under 35 U.S.C. 154(b) by 0 days.

(21) Appl. No.: 13/219,113

(22) Filed: Aug. 26, 2011

(65) Prior Publication Data

US 2013/0048660 A1 Feb. 28, 2013

(51) Int. Cl.
*B65D 43/14* (2006.01)
*A61B 19/02* (2006.01)

(52) U.S. Cl.
CPC ....... *A61B 19/0287* (2013.01); *A61B 2019/021* (2013.01); *A61B 2019/0229* (2013.01); *A61B 2019/0232* (2013.01)

(58) Field of Classification Search
CPC .............. A61M 5/002; A61B 19/0288; A61B 2019/021; A61B 2019/0213; A61B 2019/0209; A61B 2019/0247; A61B 2019/0245; B65F 1/10
USPC .......... 220/810, 229, 908, 910; 206/364–366, 206/370, 63.5, 438; 232/47–48, 28, 62, 52, 232/54, 44
See application file for complete search history.

(56) References Cited

U.S. PATENT DOCUMENTS

| | | | |
|---|---|---|---|
| 830,231 A * | 9/1906 | Homme | 232/47 |
| 1,111,031 A * | 9/1914 | Petri | 232/48 |
| 3,452,368 A * | 7/1969 | Couper | 4/484 |
| 4,488,643 A | 12/1984 | Pepper | |
| 4,502,606 A | 3/1985 | Shillington et al. | |
| 4,600,112 A | 7/1986 | Shillington et al. | |
| 4,609,117 A * | 9/1986 | Pamment | 220/252 |
| 4,625,877 A | 12/1986 | Hoch | |
| 4,667,821 A | 5/1987 | Shillington | |
| 4,674,676 A | 6/1987 | Sandel et al. | |
| 4,702,385 A | 10/1987 | Shillington et al. | |
| D292,777 S | 11/1987 | Shillington et al. | |
| 4,715,498 A | 12/1987 | Hanifl | |

(Continued)

FOREIGN PATENT DOCUMENTS

| | | |
|---|---|---|
| CA | 1093986 | 1/1981 |
| CA | 2072100 | 5/1991 |

(Continued)

OTHER PUBLICATIONS

Combined Search and Examination Report for GB Appl. No. 1215090.0 dated Dec. 5, 2012, 5 pages.

*Primary Examiner* — Anthony Stashick
*Assistant Examiner* — James M Van Buskirk
(74) *Attorney, Agent, or Firm* — Michael Best & Friedrich LLP

(57) ABSTRACT

A container for disposing of waste includes a receptacle and a first pivoting member functionally associated with the receptacle. The first pivoting member includes a first disposal surface. A second pivoting member functionally associated with the receptacle includes a second disposal surface. The second pivoting member is operatively coupled to the first pivoting member such that waste deposited on either the first disposal surface or the second disposal surface causes concurrent counter rotation of both the first pivoting member and the second pivoting member to dispose of the waste into the receptacle.

18 Claims, 19 Drawing Sheets

(56) References Cited

U.S. PATENT DOCUMENTS

| | | | |
|---|---|---|---|
| 4,736,860 A | 4/1988 | Bemis | |
| 4,842,138 A | 6/1989 | Sandel et al. | |
| 4,844,245 A | 7/1989 | Bennett | |
| D304,493 S | 11/1989 | Bemis | |
| 4,890,733 A * | 1/1990 | Anderson | 206/365 |
| 4,903,832 A | 2/1990 | Stewart | |
| 4,925,048 A | 5/1990 | Noack | |
| 4,946,064 A * | 8/1990 | VanCucha | 220/795 |
| RE33,413 E | 10/1990 | Hanifl | |
| 4,972,950 A | 11/1990 | Shillington | |
| 4,984,686 A | 1/1991 | Shillington | |
| 5,024,326 A | 6/1991 | Sandel et al. | |
| 5,024,327 A | 6/1991 | Shillington | |
| D318,159 S | 7/1991 | Noack | |
| 5,058,764 A | 10/1991 | Gaba | |
| 5,076,429 A | 12/1991 | Patrick et al. | |
| 5,080,251 A * | 1/1992 | Noack | 206/366 |
| 5,103,997 A | 4/1992 | Shillington et al. | |
| 5,107,990 A | 4/1992 | Wicherski et al. | |
| 5,147,055 A * | 9/1992 | Samson et al. | 220/259.2 |
| 5,154,345 A | 10/1992 | Shillington | |
| D332,680 S | 1/1993 | Ramirez | |
| 5,178,322 A | 1/1993 | Shillington | |
| 5,184,720 A | 2/1993 | Packer et al. | |
| 5,222,599 A | 6/1993 | Boyce | |
| 5,240,108 A | 8/1993 | Tonna | |
| 5,249,680 A | 10/1993 | Shillington | |
| 5,346,086 A | 9/1994 | Harris | |
| D351,906 S | 10/1994 | Marsh | |
| 5,387,735 A * | 2/1995 | Ponsi et al. | 588/249 |
| 5,394,982 A | 3/1995 | Sawaya | |
| 5,395,008 A | 3/1995 | Bemis et al. | |
| 5,402,887 A | 4/1995 | Shillington | |
| 5,413,243 A | 5/1995 | Bemis et al. | |
| 5,415,315 A | 5/1995 | Ramirez | |
| 5,419,435 A | 5/1995 | Perzan et al. | |
| 5,423,450 A | 6/1995 | Shillington et al. | |
| 5,465,841 A | 11/1995 | Wilson et al. | |
| 5,474,180 A | 12/1995 | Robinson et al. | |
| 5,474,181 A | 12/1995 | Shillington | |
| 5,494,186 A | 2/1996 | Marsh | |
| 5,570,783 A * | 11/1996 | Thorne et al. | 206/366 |
| 5,573,113 A | 11/1996 | Shillington et al. | |
| D376,647 S | 12/1996 | Marsh et al. | |
| 5,603,404 A | 2/1997 | Nazare et al. | |
| 5,605,245 A | 2/1997 | Bemis et al. | |
| 5,630,506 A | 5/1997 | Thorne et al. | |
| 5,647,502 A | 7/1997 | Marsh | |
| 5,667,092 A | 9/1997 | Julius et al. | |
| 5,740,909 A | 4/1998 | Nazare et al. | |
| 5,772,059 A | 6/1998 | McCord | |
| 5,848,692 A | 12/1998 | Thorne et al. | |
| 5,947,285 A | 9/1999 | Gaba et al. | |
| 5,947,950 A | 9/1999 | Shillington et al. | |
| D418,977 S | 1/2000 | Streich | |
| 6,024,216 A | 2/2000 | Shillington et al. | |
| 6,062,001 A | 5/2000 | Kunik | |
| 6,065,272 A * | 5/2000 | Lecomte | 53/576 |
| 6,213,296 B1 | 4/2001 | Streich et al. | |
| 6,250,465 B1 | 6/2001 | Daniels et al. | |
| D445,116 S | 7/2001 | Evans et al. | |
| D447,233 S | 8/2001 | Bickel et al. | |
| D448,167 S | 9/2001 | Pangerc et al. | |
| 6,283,909 B1 | 9/2001 | Sharp | |
| D451,195 S | 11/2001 | Daniels et al. | |
| D474,840 S | 5/2003 | Crawford | |
| 6,561,352 B2 | 5/2003 | Sherman et al. | |
| D478,664 S | 8/2003 | Moats et al. | |
| D478,701 S | 8/2003 | Panek, Jr. | |
| D482,448 S | 11/2003 | Crawford | |
| D485,906 S | 1/2004 | Danssaert et al. | |
| 6,685,017 B2 | 2/2004 | Erickson | |
| 6,712,207 B2 | 3/2004 | Panek, Jr. et al. | |
| 6,792,662 B2 | 9/2004 | Samuel | |
| 6,889,831 B2 * | 5/2005 | Pike | 206/366 |
| 6,923,318 B1 | 8/2005 | Erickson et al. | |
| 7,048,133 B2 | 5/2006 | Pangerc et al. | |
| 7,108,148 B2 * | 9/2006 | Lu | 220/263 |
| 7,114,629 B2 | 10/2006 | Panek, Jr. | |
| 7,159,714 B2 | 1/2007 | Wilkinson et al. | |
| 7,243,792 B2 | 7/2007 | Panek, Jr. et al. | |
| 7,344,027 B2 | 3/2008 | Erickson et al. | |
| 7,364,049 B2 | 4/2008 | Panek, Jr. | |
| 7,445,116 B2 | 11/2008 | Dansaert et al. | |
| 7,516,844 B2 | 4/2009 | Erickson et al. | |
| D591,859 S | 5/2009 | Stark et al. | |
| 7,537,117 B2 | 5/2009 | Roesler | |
| 7,556,149 B2 | 7/2009 | Erickson et al. | |
| 7,596,844 B2 | 10/2009 | Japuntich et al. | |
| 7,600,638 B2 | 10/2009 | Finnestad et al. | |
| 7,600,639 B2 | 10/2009 | Japuntich et al. | |
| 7,694,811 B2 | 4/2010 | Brown et al. | |
| 7,694,822 B2 | 4/2010 | Sullivan et al. | |
| 7,721,886 B2 | 5/2010 | Erickson et al. | |
| 7,780,046 B1 | 8/2010 | Lowe | |
| 7,784,167 B2 | 8/2010 | Panek, Jr. | |
| 7,784,642 B2 | 8/2010 | Gavin et al. | |
| 7,789,230 B2 | 9/2010 | Klein | |
| 7,877,849 B2 | 2/2011 | Panek, Jr. et al. | |
| 7,891,487 B2 | 2/2011 | Erickson et al. | |
| 2002/0024223 A1 | 2/2002 | Bolduc et al. | |
| 2003/0183546 A1 | 10/2003 | Crawford | |
| 2003/0213714 A1 | 11/2003 | Moats et al. | |
| 2005/0103662 A1 | 5/2005 | Iske et al. | |
| 2006/0102504 A1 | 5/2006 | Phan | |
| 2007/0068832 A1 | 3/2007 | Anderson et al. | |
| 2008/0060958 A1 | 3/2008 | Iske et al. | |
| 2008/0156666 A1 | 7/2008 | Panek | |
| 2008/0156818 A1 | 7/2008 | Panek | |
| 2008/0179207 A1 | 7/2008 | Stowe et al. | |
| 2008/0217332 A1 | 9/2008 | Kleyman et al. | |
| 2009/0107998 A1 | 4/2009 | Meissen | |
| 2009/0108007 A1 | 4/2009 | Anderson et al. | |
| 2009/0114653 A1 | 5/2009 | Schenker | |
| 2009/0114671 A1 | 5/2009 | Finnestad et al. | |
| 2009/0120820 A1 | 5/2009 | Iske et al. | |
| 2009/0120821 A1 | 5/2009 | Japuntich et al. | |
| 2009/0173744 A1 | 7/2009 | Hassell | |
| 2009/0294312 A1 | 12/2009 | Hitson | |
| 2010/0032441 A1 | 2/2010 | Stark et al. | |
| 2010/0155400 A1 | 6/2010 | Finnestad et al. | |
| 2011/0147385 A1 * | 6/2011 | Forrest | 220/324 |

FOREIGN PATENT DOCUMENTS

| | | |
|---|---|---|
| CA | 2071919 | 8/1991 |
| CA | 2038022 | 9/1991 |
| CA | 1291097 | 10/1991 |
| CA | 1304054 | 6/1992 |
| CA | 1304334 | 6/1992 |
| CA | 1306726 | 8/1992 |
| CA | 2038595 | 9/1992 |
| CA | 2122444 | 5/1993 |
| CA | 2114987 | 10/1994 |
| CA | 2164727 | 12/1994 |
| CA | 2213487 | 10/1996 |
| CA | 2216553 | 10/1996 |
| CA | 2147467 | 11/1997 |
| CA | 2277047 | 7/1998 |
| CA | 2360043 | 7/2000 |
| CA | 2293224 | 6/2001 |
| CA | 2082271 | 5/2003 |
| CA | 2484008 | 11/2003 |
| CA | 2555784 | 9/2005 |
| CA | 2370720 | 12/2005 |
| CA | 2526000 | 5/2006 |
| CA | 2539323 | 9/2006 |
| CA | 2538278 | 10/2006 |
| CA | 2606730 | 11/2006 |
| CA | 2607032 | 11/2006 |
| CA | 2553466 | 1/2007 |
| CA | 2685464 | 11/2008 |
| CA | 2642062 | 4/2009 |
| CA | 2640252 | 5/2009 |

(56) References Cited

FOREIGN PATENT DOCUMENTS

| | | |
|---|---|---|
| CA | 2647659 | 7/2009 |
| CA | 2718714 | 9/2009 |
| CA | 2674255 | 2/2010 |
| CA | 2739922 | 4/2010 |
| EP | 0221378 | 5/1987 |
| EP | 0697344 | 2/1996 |
| EP | 0808782 | 11/1997 |
| EP | 0842641 | 5/1998 |
| EP | 0860174 | 8/1998 |
| ES | 2116524 | 7/1998 |
| GB | 2087360 | 5/1982 |
| GB | 2261359 | 5/1993 |
| GB | 2286582 | 8/1995 |
| GB | 2355178 | 4/2001 |
| GB | 2398225 | 8/2004 |
| WO | 9220450 | 11/1992 |
| WO | 02085757 | 10/2002 |

* cited by examiner

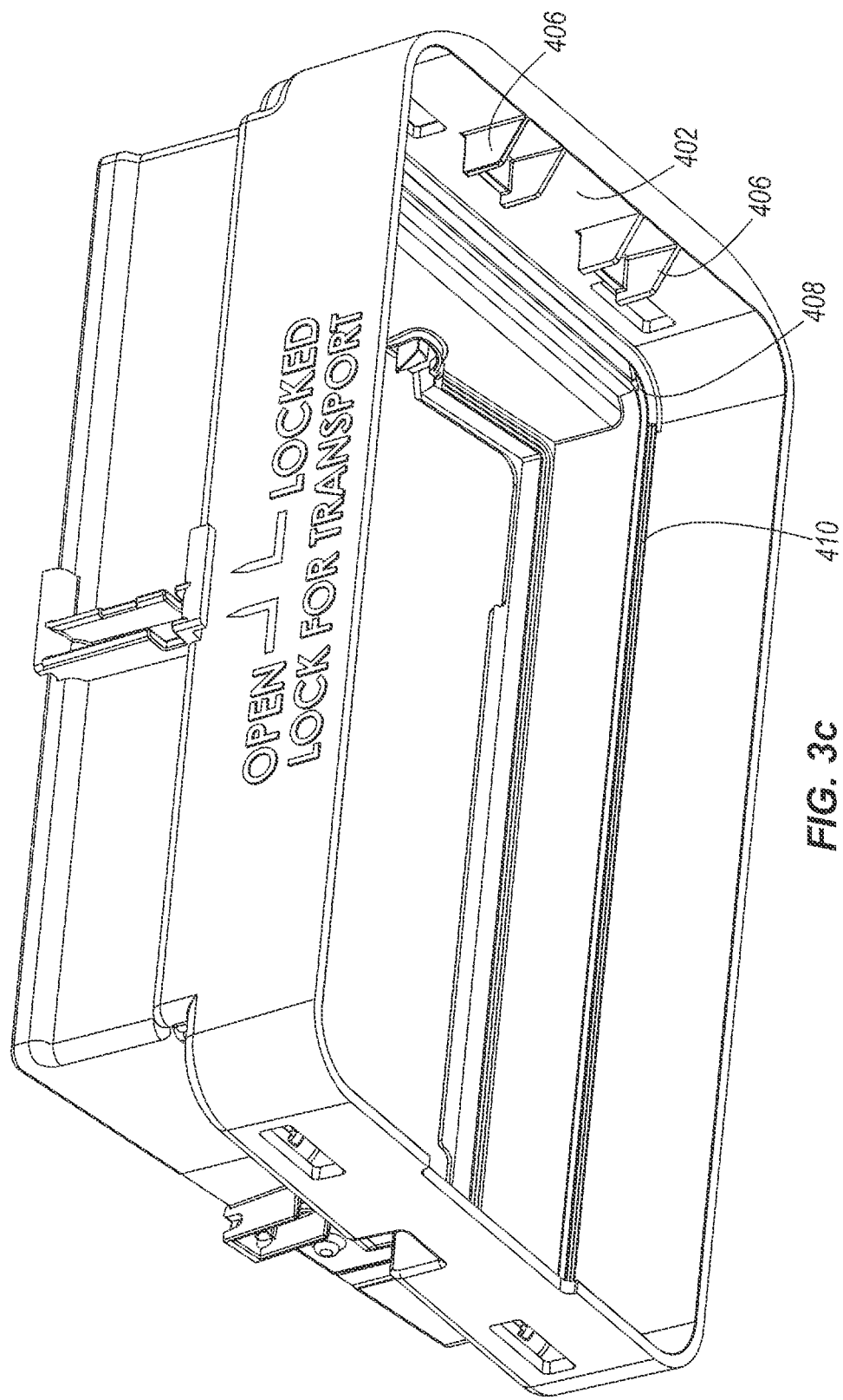

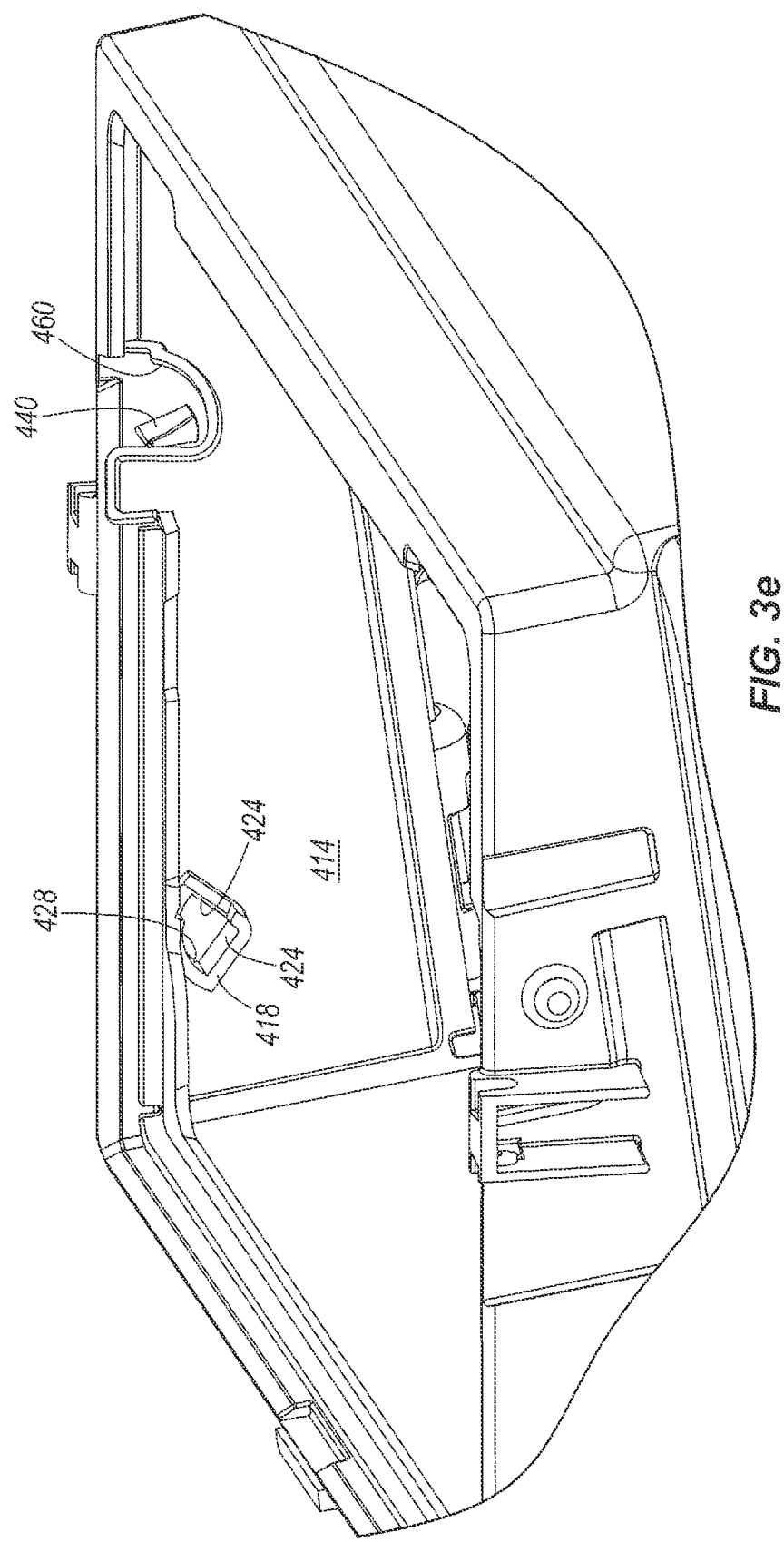

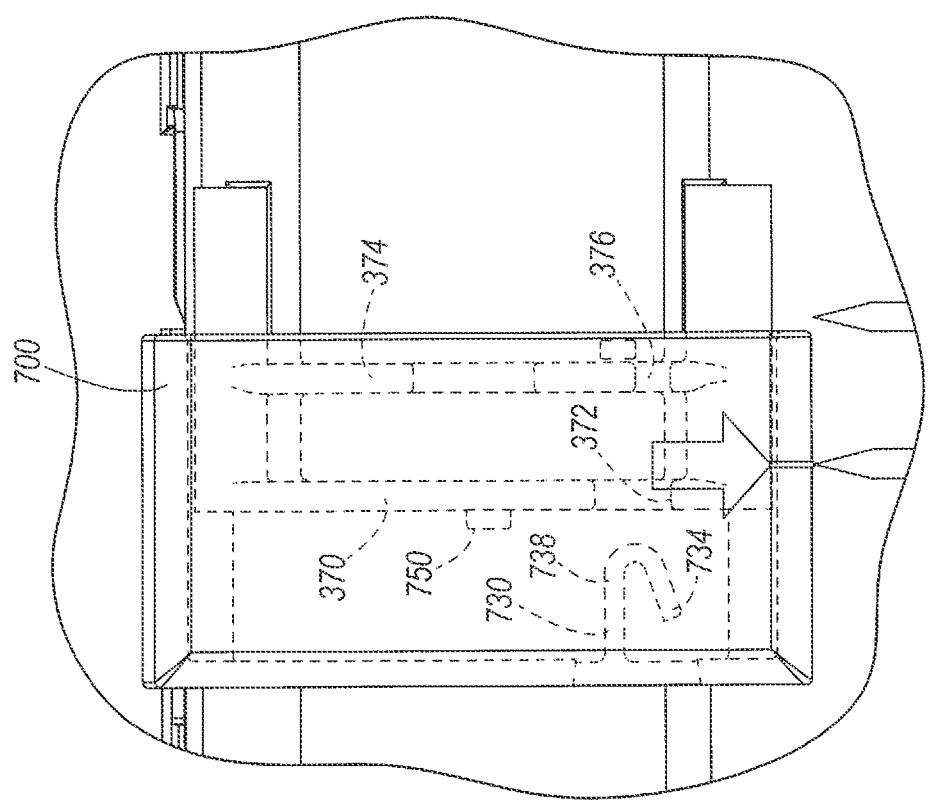
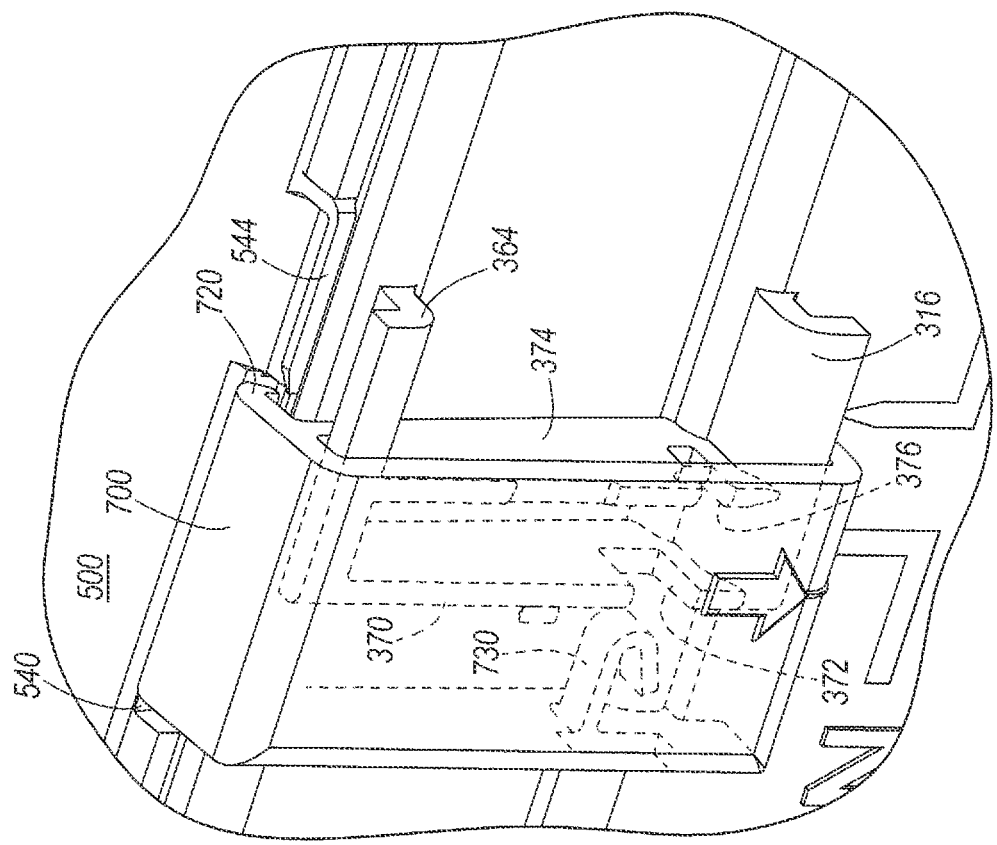

WASTE CONTAINER ASSEMBLY

BACKGROUND

The present invention relates to the disposal of waste, and more particularly to a waste container assembly for the disposal of medical waste products.

SUMMARY

The disposal of medical waste is a concern for hospitals and medical clinics. In particular, certain items of waste are not reusable and at the same time may present a danger to medical staff and patients if accessible due to sharp edges or pointed tips, e.g., syringes. These waste items need to be stored in a safe manner that reduces the chance of someone accidentally coming into contact with the waste while hindering those who may be purposefully trying to obtain waste products, such as used syringes for illicit drug use. A waste container assembly providing limited access to the contents during the act of disposing of the waste, and while the waste is stored and awaiting permanent disposal, is desired.

The present invention provides, in one aspect, a container for disposing of waste. The container includes a receptacle and a first pivoting member functionally associated with the receptacle. The first pivoting member includes a first disposal surface. A second pivoting member is functionally associated with the receptacle and includes a second disposal surface. The second pivoting member is operatively coupled to the first pivoting member such that waste deposited on either the first disposal surface or the second disposal surface causes concurrent counter rotation of both the first pivoting member and the second pivoting member to dispose of the waste into the receptacle.

Other aspects of the invention will become apparent by consideration of the detailed description and accompanying drawings.

BRIEF DESCRIPTION OF THE DRAWINGS

FIG. 2b is a partial perspective view showing a second side of the receptacle of FIG. 2a.

FIG. 3b is a perspective view showing a second exterior side of the mounting member of FIG. 3a.

FIG. 3c is a perspective view showing a first interior side of the mounting member of FIG. 3a.

FIG. 3e is a partial perspective view showing additional interior side features of the mounting member of FIG. 3a.

FIG. 4a is a perspective view of a pivot projection of the mounting member of FIG. 3a.

FIG. 4b is a second perspective view of the pivot projection of FIG. 4a.

FIG. 5b is a second perspective view of the first pivoting member of FIG. 5a.

FIG. 6b is a side view of the second pivoting member of FIG. 6a.

FIG. 6c is a second perspective view of the second pivoting member of FIG. 6a.

FIG. 7a is a perspective view of the first and second pivoting members of FIGS. 5a and 6a.

FIG. 7b is a perspective view of the first and second pivoting members of FIGS. 5a and 6a with the mounting member of FIG. 3a.

FIG. 10a is a partial perspective view of the locking latch of FIG. 9 in an open position.

FIG. 10b is a partial front view of the locking latch of FIG. 10a.

FIG. 11b is a partial front view of the locking latch of FIG. 11a.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
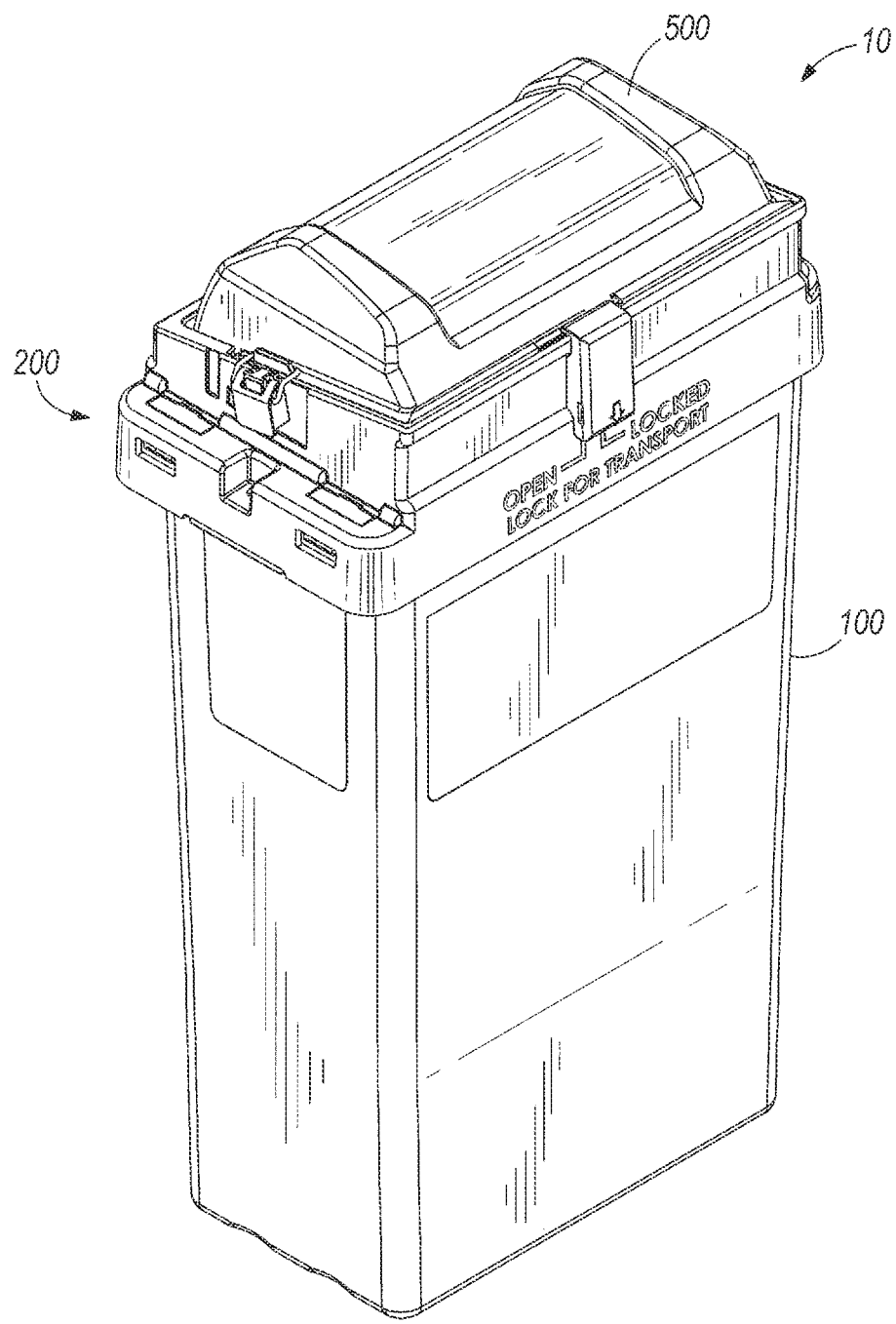
FIG. 1 is a perspective view of a waste container assembly embodying the present invention.
Figure 2B:
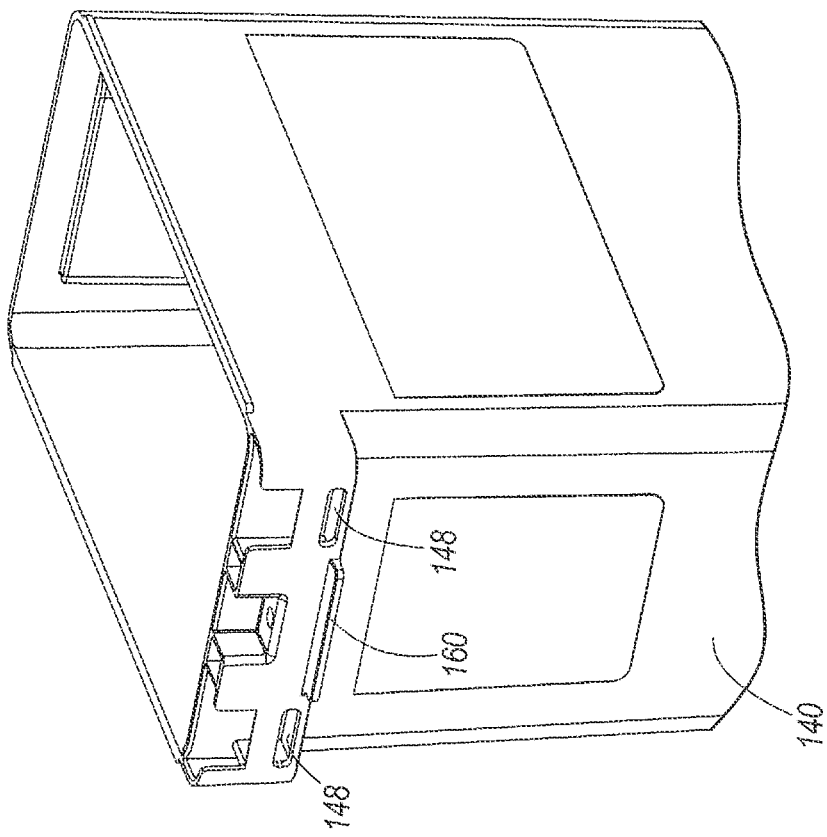
Figure 2A:
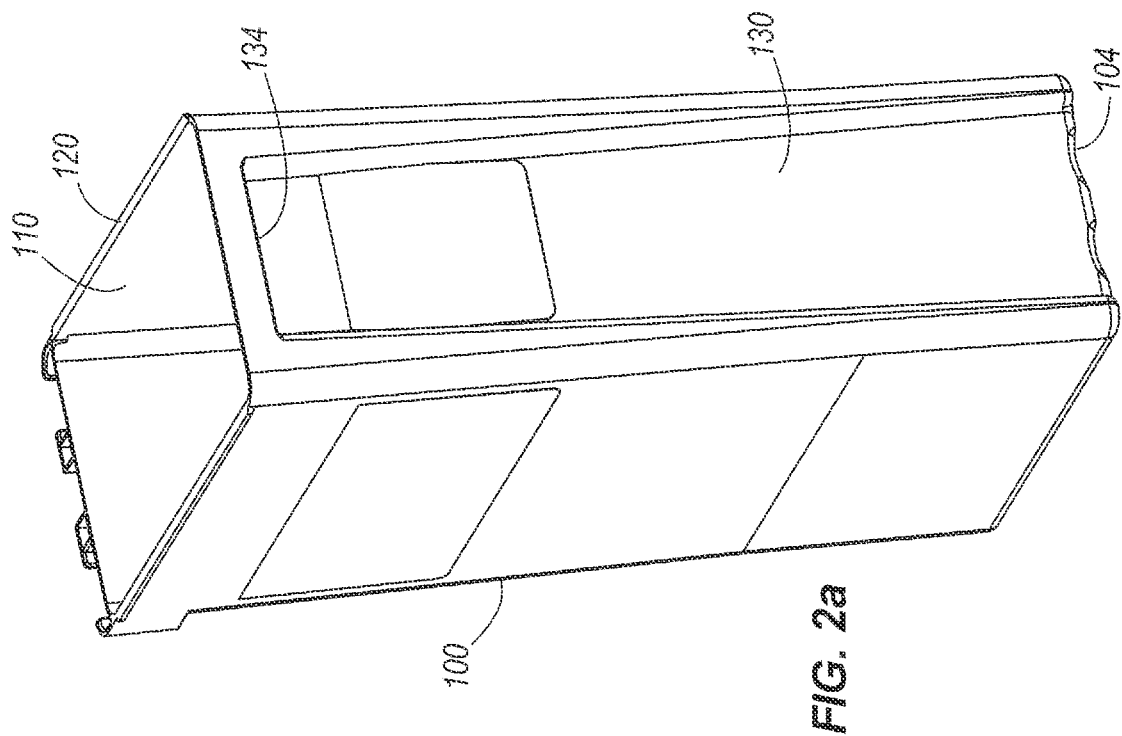
FIG. 2a is a perspective view showing a first side of a receptacle of the waste container assembly of FIG. 1.

FIG. 1 illustrates a container assembly 10 for disposing of waste. The container assembly 10 includes a receptacle 100 and a disposal assembly 200. The receptacle 100 is a vessel with a specific capacity for holding a quantity of items disposed via the disposal assembly 200. In the presently described embodiment, for example, the receptacle 100 is a four-sided, four-gallon sized receptacle. Other sizes and/or shapes are of course contemplated depending on the particular needs of the application. Referring to FIG. 2a, the receptacle 100 includes a bottom 104 that can be supported on a relatively flat surface, such as a floor. Alternatively, the receptacle 100 (and the assembly 10) can be mounted to a wall, with a mounting bracket or similar mounting assembly (not shown) that partially or wholly encloses the receptacle 100. The receptacle 100 can be further tapered to accommodate various mounting configurations. The top of the receptacle 100 defines a receptacle opening 110 bounded by a perimeter 120 through which waste is disposed.

A first side 130 of the receptacle 100 includes additional surface features, for example one or more edges 134 for securing a mounting member 300, described below (see FIG. 3a), and for facilitating manual transport of the receptacle 100. Referring to FIG. 2b, a second side 140 of the receptacle 100 receives latches 144 of the mounting member 300 (see FIG. 3b) for removably securing the mounting member 300. The latches 144 are secured and released through apertures 148. A lip 160 facilitates transport or manipulation of the receptacle 100 and/or the entire container assembly 10.

Figure 3A:
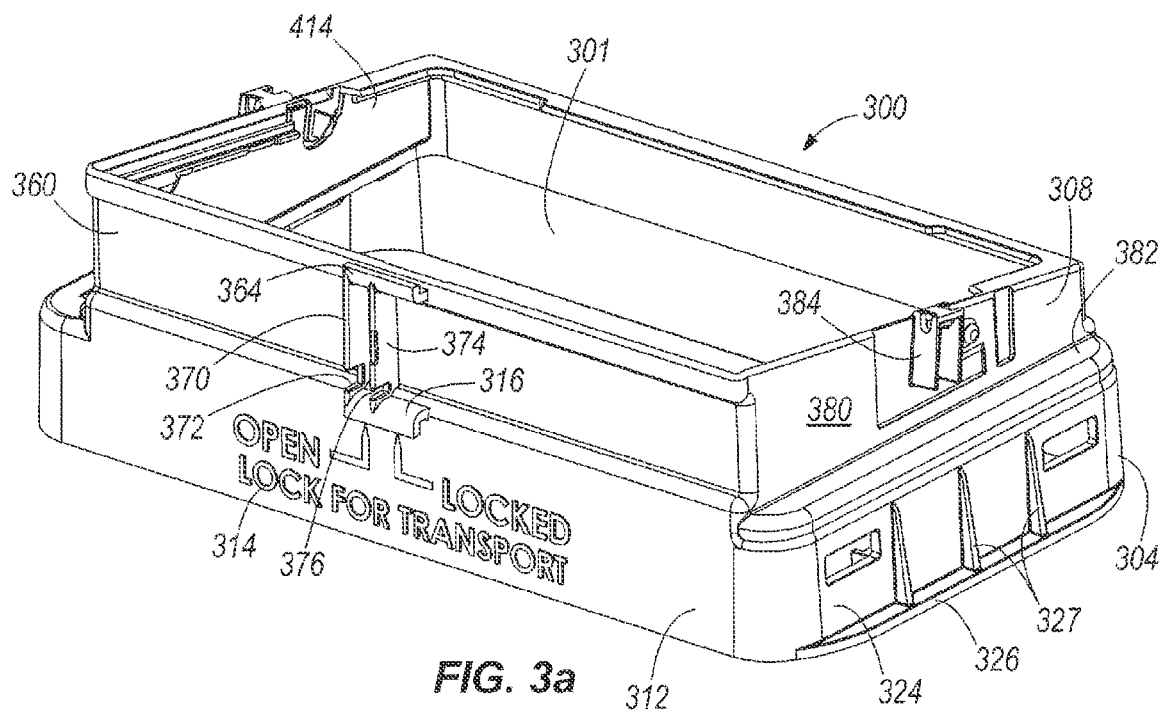
FIG. 3a is a perspective view showing a first exterior side of a mounting member of the waste container of FIG. 1.

Referring to FIG. 3a, the mounting member 300 fits over the perimeter 120 of the receptacle 100 and defines an opening 301. The mounting member 300 includes a bottom portion 304 for attachment to the receptacle 100 and a top portion 308.

The bottom portion 304 includes four external faces to match the geometry of the perimeter 120. As illustrated in FIG. 3a, a generally planar front face 312 includes a lower lip 316 for securing a bottom edge of a locking latch 700 (described more fully below, see FIGS. 9-11b) to the mounting member 300. The front face 312 includes a descriptor or indicia 314 to alert a user of the container assembly 10 of the current position of the locking mechanism. A right face 324 includes a lift member 326 with supporting braces 327 to aid in lifting the mounting member 300 from the receptacle 100.

Figure 3B:
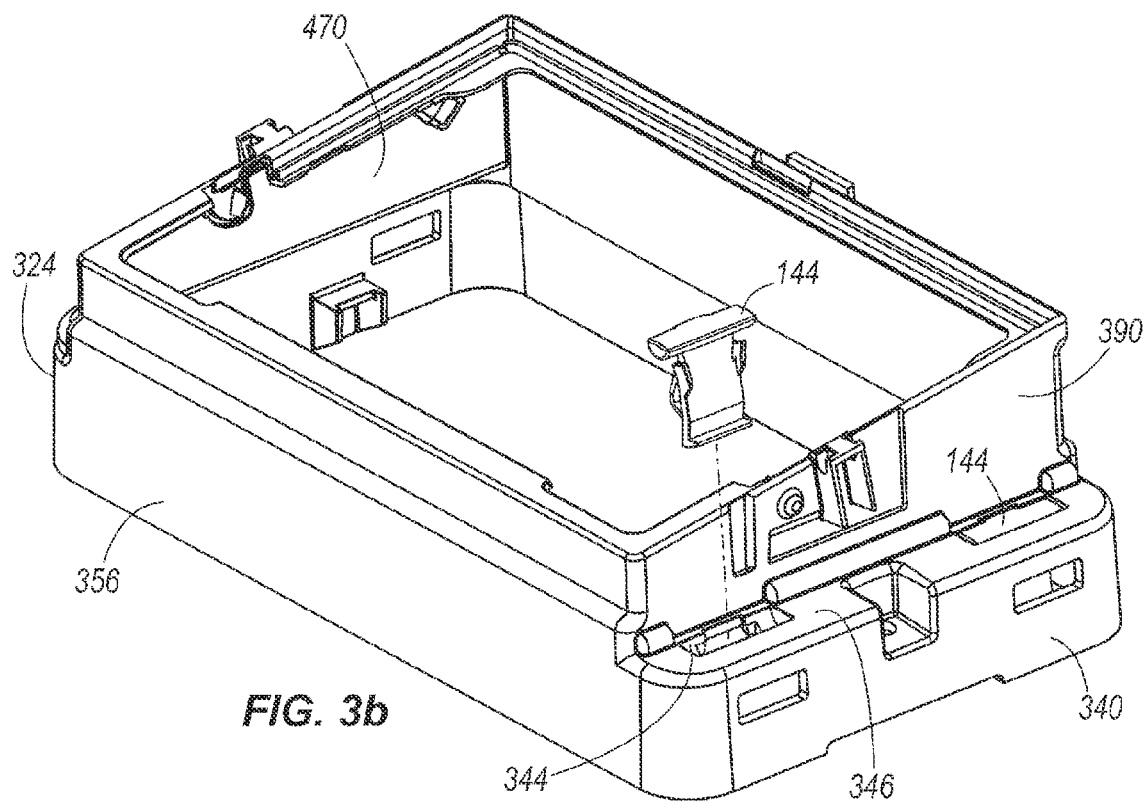

Referring to FIG. 3b, a left face 340 includes slots 344 formed in a ledge 346 for receiving the latches 144 to removably secure the receptacle 100 to the mounting member 300. A generally planar rear surface 356 extends from the right face 324 to the left face 340.

Referring again to FIGS. 3a and 3b, the top portion 308 includes a front face 360. The front face 360 includes an upper lip 364 for securing a top edge of the locking latch 700 to a first pivoting member 500 further described below (see FIGS. 5a-5b). Extending from the front face 360 are a locking engagement member 370 with an opening 372 and a locking release member 374 with an opening 376, all of which will be further described in conjunction with the locking mechanism illustrated in FIGS. 10a-11b. A right face 380 as illustrated in FIG. 3a tapers from the front to the rear and is separated from the right face 324 of the lower portion 304 by a ledge 382. A latch mount 384 is affixed to and extends from the right face 380 and supports a closure latch 580 described below and illustrated in FIG. 5c. A left face 390 as shown in FIG. 3b is substantially similar in description to the right face 380, with the left face 390 similarly tapering from front to rear.

Figure 3D:
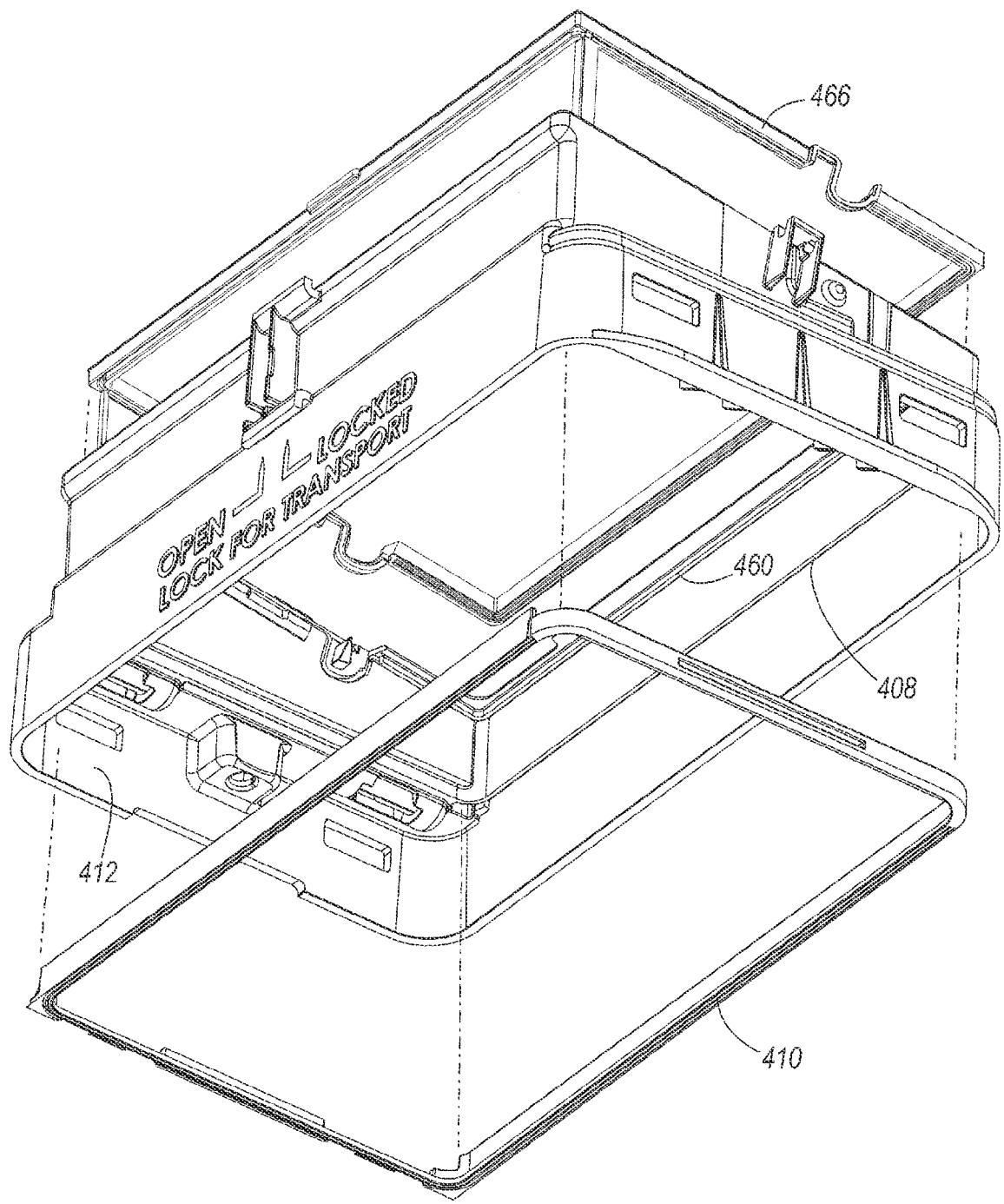
FIG. 3d is an exploded perspective view showing a second interior side of the mounting member of FIG. 3a and associated gaskets.

Internally, as shown in FIG. 3c, a lower right interior face 402 of the mounting member 300 includes one or more brackets 406 that fit under the edges 134 of the receptacle 100 (FIG. 2a) for securing the mounting member 300 to the receptacle 100. An internal margin 408 provides a seating surface for a lower gasket 410 that provides a seal between the mounting member 300 and the receptacle 100. Referring to FIG. 3d, a lower internal left face 412 is illustrated for reference and shows the opposing interior surface of the features described with respect to FIG. 3b. The lower gasket 410 is also shown separately for clarity.

Figure 4A:
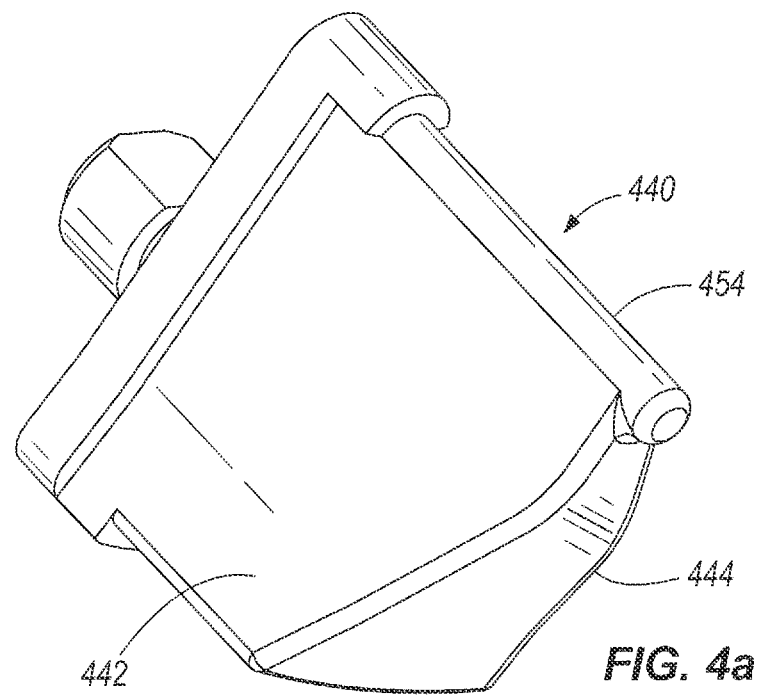
Figure 4B:
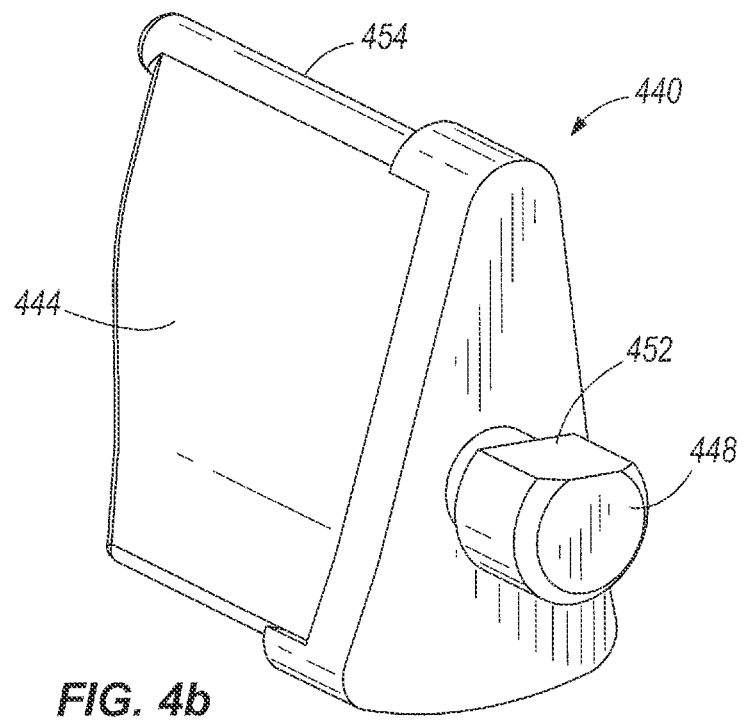
Figure 6A:
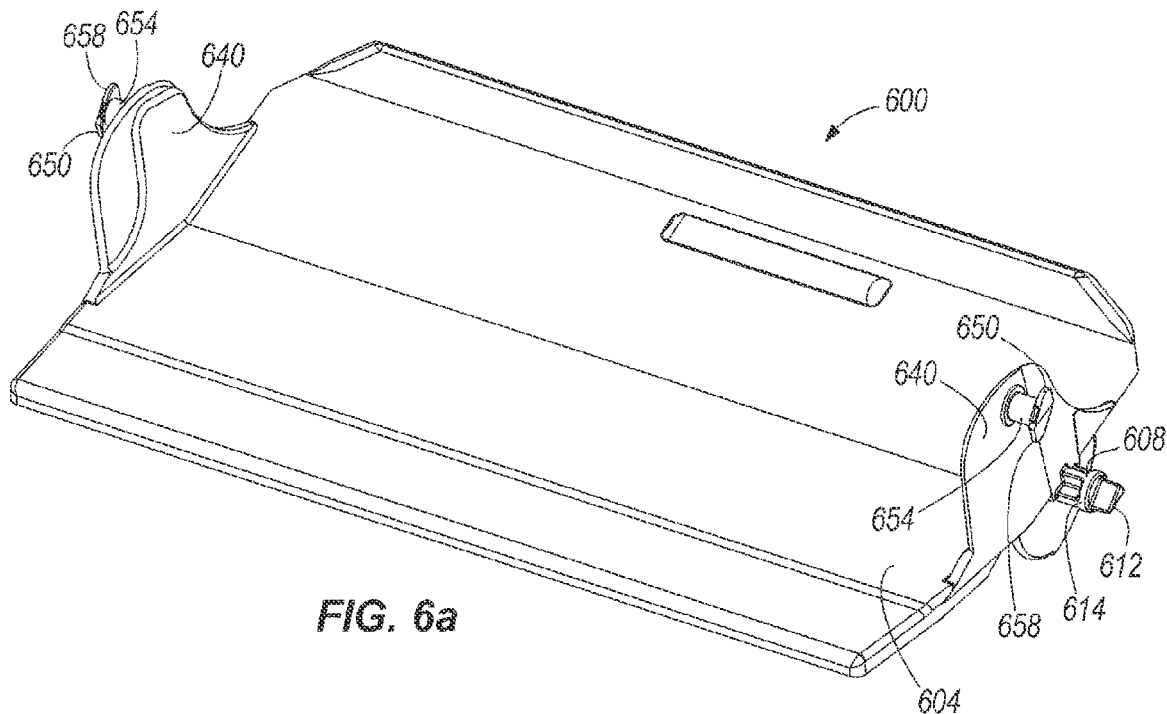
FIG. 6a is a perspective view of a second pivoting member of the waste container assembly of FIG. 1.
Figure 6B:
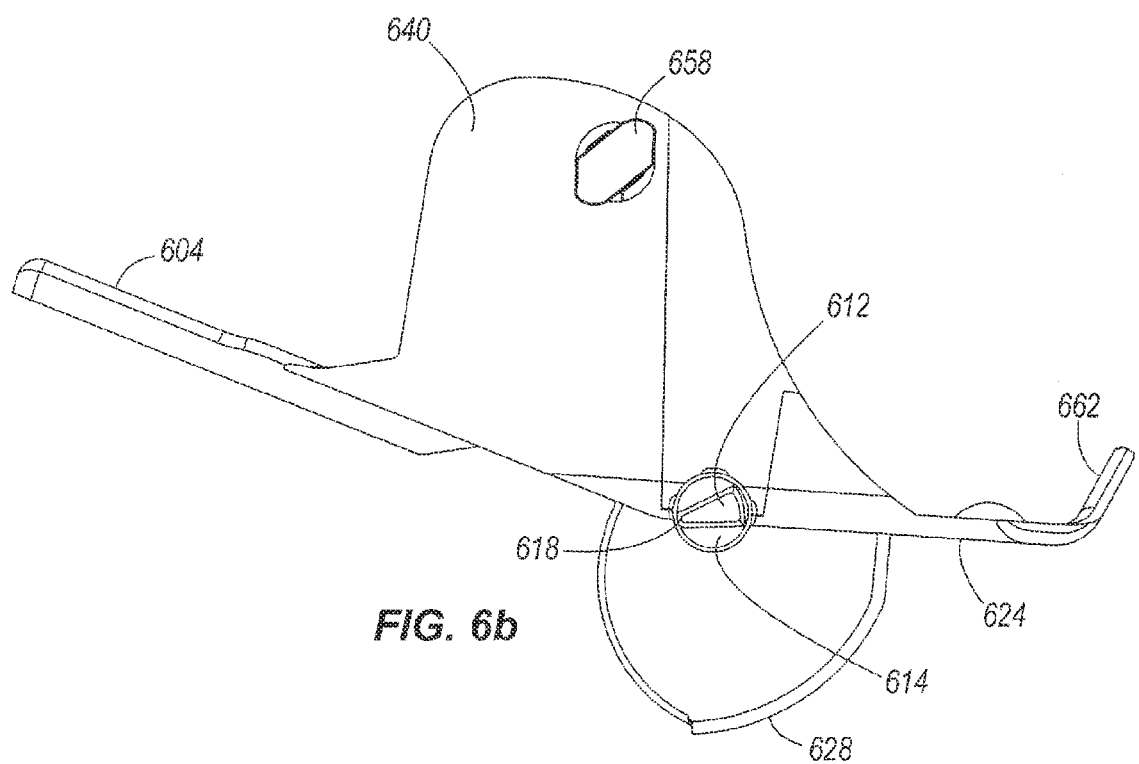
Figure 6C:
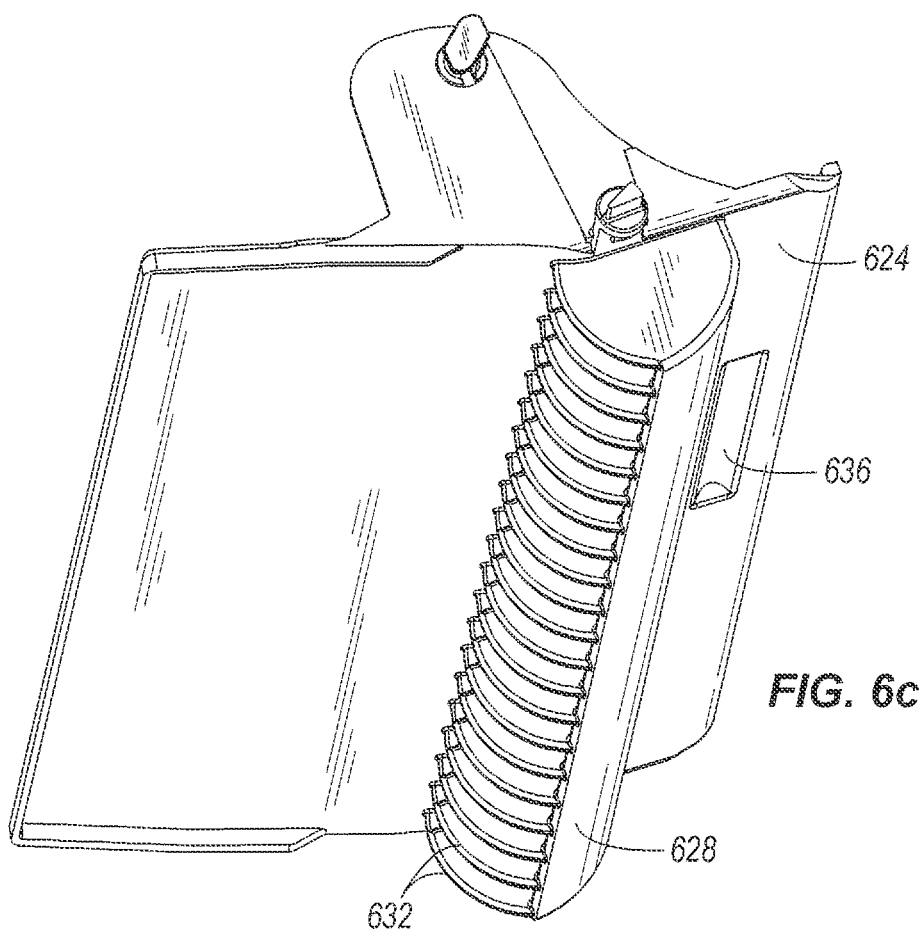

An upper left interior face 414, shown in FIG. 3e, includes a seat 418 into which a pivot projection 612 of a pivoting member 600, to be further described and shown in FIGS. 6a-6c, is situated. The seat 418 includes two seating surfaces 424 providing the limits of pivoting motion of the pivot projection 612. An upper arcuate surface 428 further assists in preventing translation of the pivot projection 612 of the pivoting member 600 with respect to the mounting member 300. A pivot projection 440 extends from the left interior face 414 toward the interior of the mounting member 300 for pivotal movement of the pivoting member 500. As shown in FIG. 4a, the pivot projection 440 presents a generally wedge shape with sides 442, 444. The pivot projection 440 can be permanently attached to the upper left interior face 414 or can be inserted into the face 414. As illustrated in FIG. 4b, a generally circular knob 448 includes a flat surface 452 to prevent rotation of the pivot projection 440 within the mounting member 300. The sides 442, 444, meet to form a pivot surface 454.

Referring to FIGS. 3d and 3e, a seal ridge 460 provides an engagement surface for an upper gasket 466. The seal ridge 460 and upper gasket 466 are shaped to partially circumscribe the pivot projection 440 to provide a closure seal when the container assembly 10 is closed and ready for transport (shown in FIG. 1), as will be further described below. An upper right interior face 470 (see FIG. 3b) is substantially similar to the upper left interior face 414.

Figure 5A:
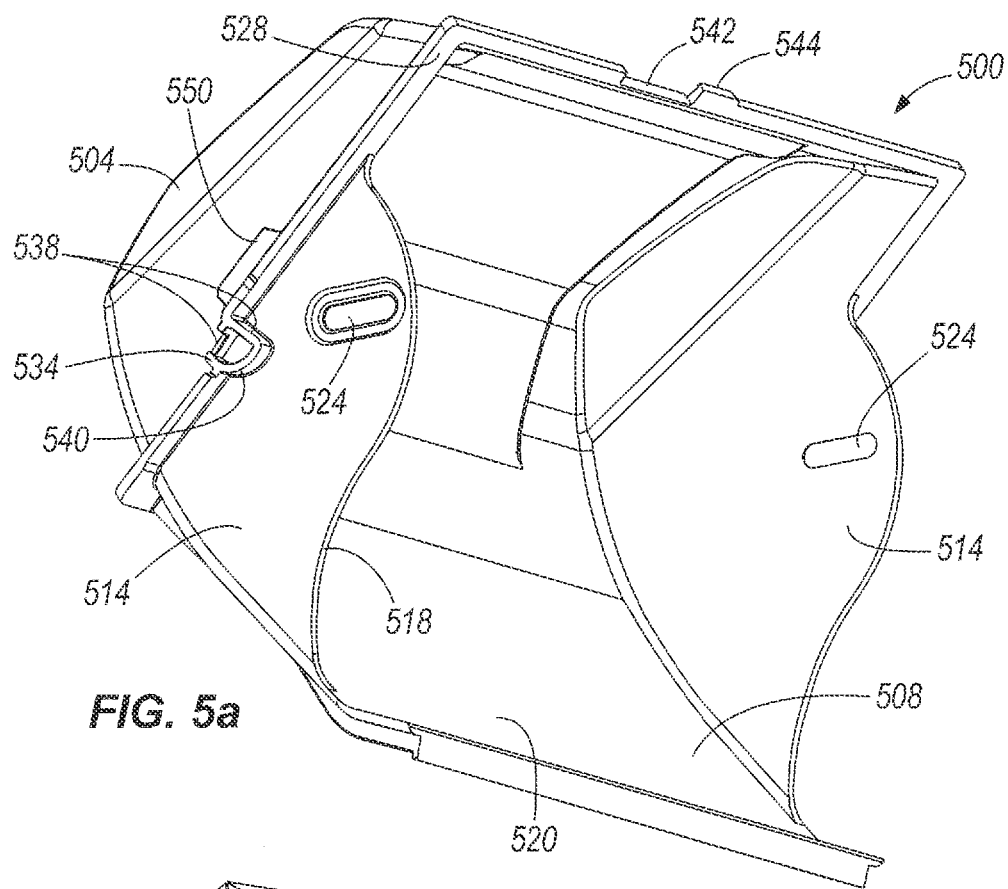
FIG. 5a is a perspective view of a first pivoting member of the waste container assembly of FIG. 1.

Referring to FIG. 5a, the first pivoting member 500, which is functionally associated with the receptacle 100 via the mounting member 300, includes a generally curved hood portion 504 merging with a disposal portion 508. Opposing sides 514 adjoin the hood portion 504 with the disposal portion 508, with each side 514 having an arcuate edge 518. A disposal surface 520 of the disposal portion 508 can have any shape suitable for the placement of waste and can be generally flat or somewhat curved. Each side 514 is formed to accommodate an opposing aperture 524, such as linear, elongated slot, the purpose of which is to be further described below.

Figure 5B:
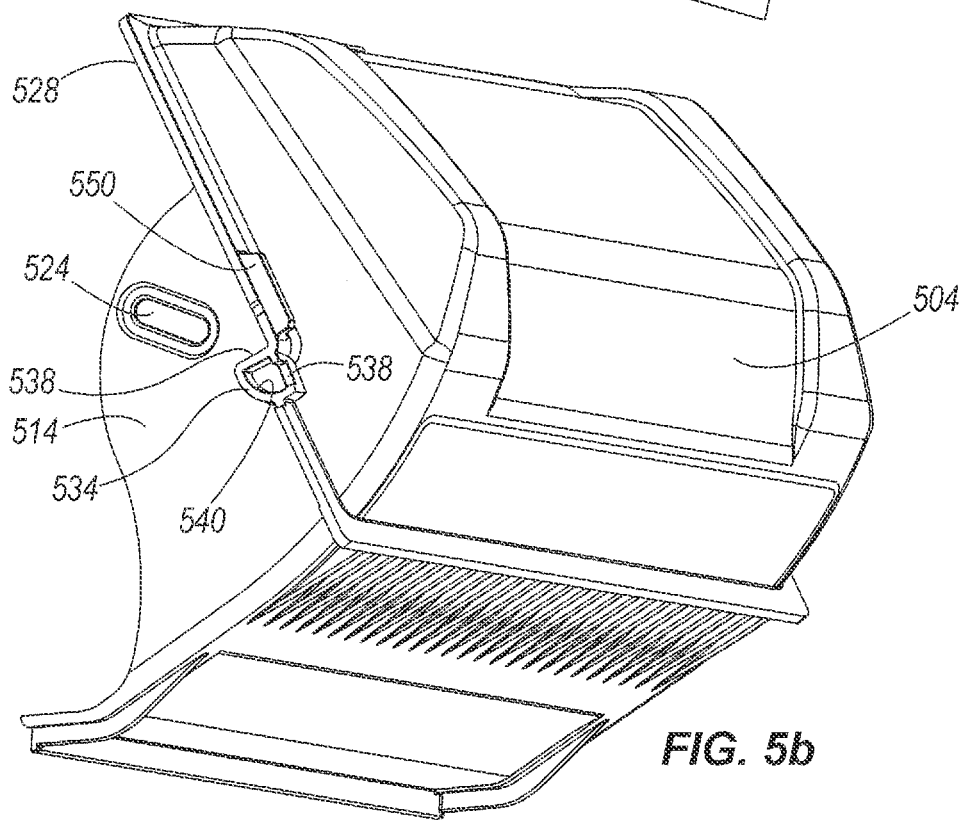

An edge or flange 528 surrounding the hood portion 504 forms a pivot seat 534 that cooperates with the pivot projection 440 of the upper left interior face 414 previously described. A second opposing pivot seat 534 on the opposite side of the pivoting member 500, as illustrated in FIG. 5b, cooperates with the pivot projection 440 of the upper right interior face 470 such that pivoting member 500 pivots about the pivot surfaces 454 of the projections 440. The range of pivoting for pivoting member 500 is limited by two seating surfaces 538 of the pivot seat 534 that limit the pivoting motion of the pivot projection 440. An arcuate surface 540 further assists in preventing translation of the pivoting member 500 with respect to the mounting member 300.

Figure 9:
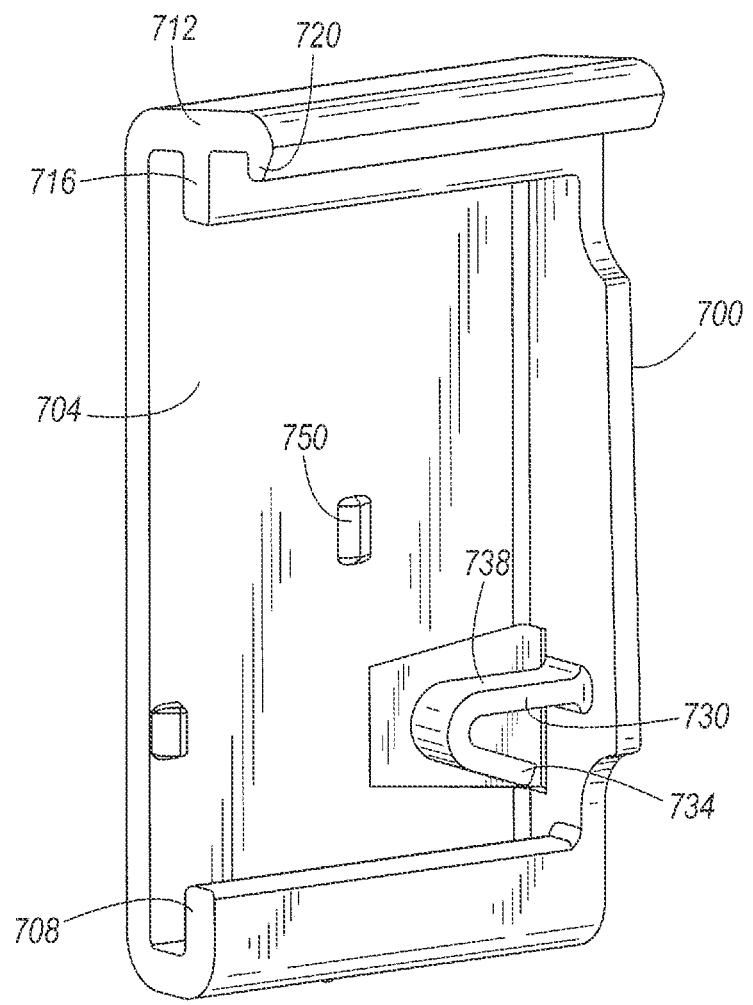
FIG. 9 is a perspective view of a locking latch of the waste container assembly embodying the present invention.

The flange 528 further acts as a sealing member when the first pivoting member 500 is in a closed position (as in FIG. 1) to limit access into the receptacle 100. A depression 542 is formed in the front side of the flange 528 to accommodate the locking latch 700 (FIG. 9). Adjacent the depression 542 is a locking lip 544 over which the locking latch 700 slides, as further explained below.

Figure 5C:
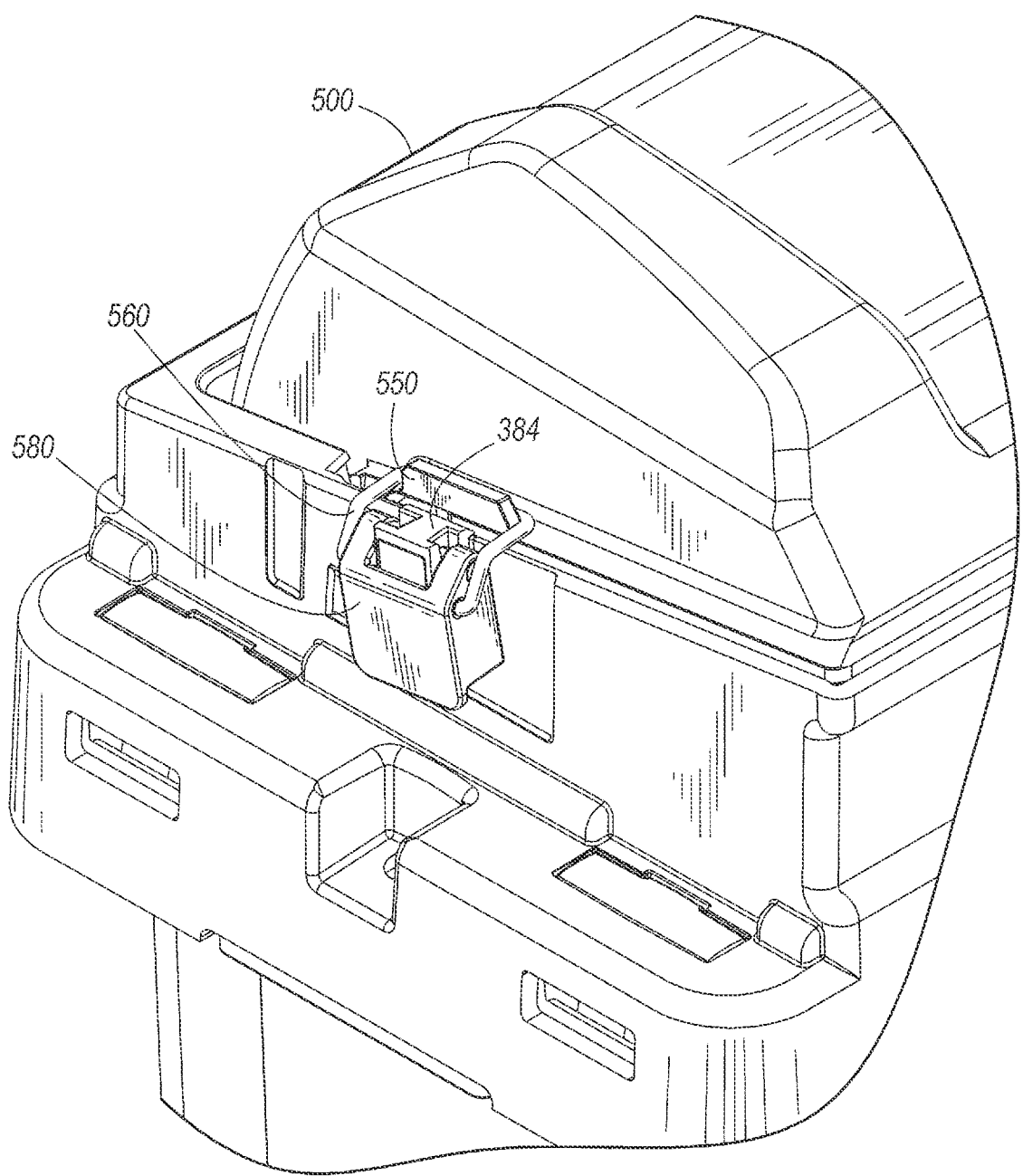
FIG. 5c is a perspective view of a closure latch of the waste container assembly of FIG. 1.

Also formed adjacent the flange 528 on both sides 514 is a tab 550 that hooks a latch loop 560 from the respective closure latch 580. As shown in FIG. 5c, the closure latch 580 is coupled to the latch mount 384 and generally functions in a conventional manner familiar to those of skill in the art. The closure latch 580 provides force that helps compress flange 528 against upper gasket 466 to form a tight seal between the first pivoting member 500 and the mounting member 300 when the first pivoting member 500 is closed and latched with the closure latches 580.

FIGS. 6a and 6b illustrate the second pivoting member 600 of the presently described embodiment. The pivoting member 600, which is functionally associated with the receptacle 100 via the mounting member 300, defines a disposal surface 604 upon which waste can be placed for disposal into the receptacle 100. A pivot arm 608 includes a generally wedge-shaped pivot projection 612 that seats within the previously described seat 418 of the upper left interior face 414 of the mounting member 300. A pivot platform 614 extends the pivot projection 612 away from the disposal surface 604 for unhindered rotation of the second pivoting member 600. A second opposing pivot arm 608 (not shown) with an identical wedge-shaped pivot projection 612 on the opposite side of the second pivoting member 600 cooperates with the seat 418 of the upper right interior face 470 such that pivoting member 600 pivots about each pivot surface 618 of the respective pivot projections 612.

Figure 7C:
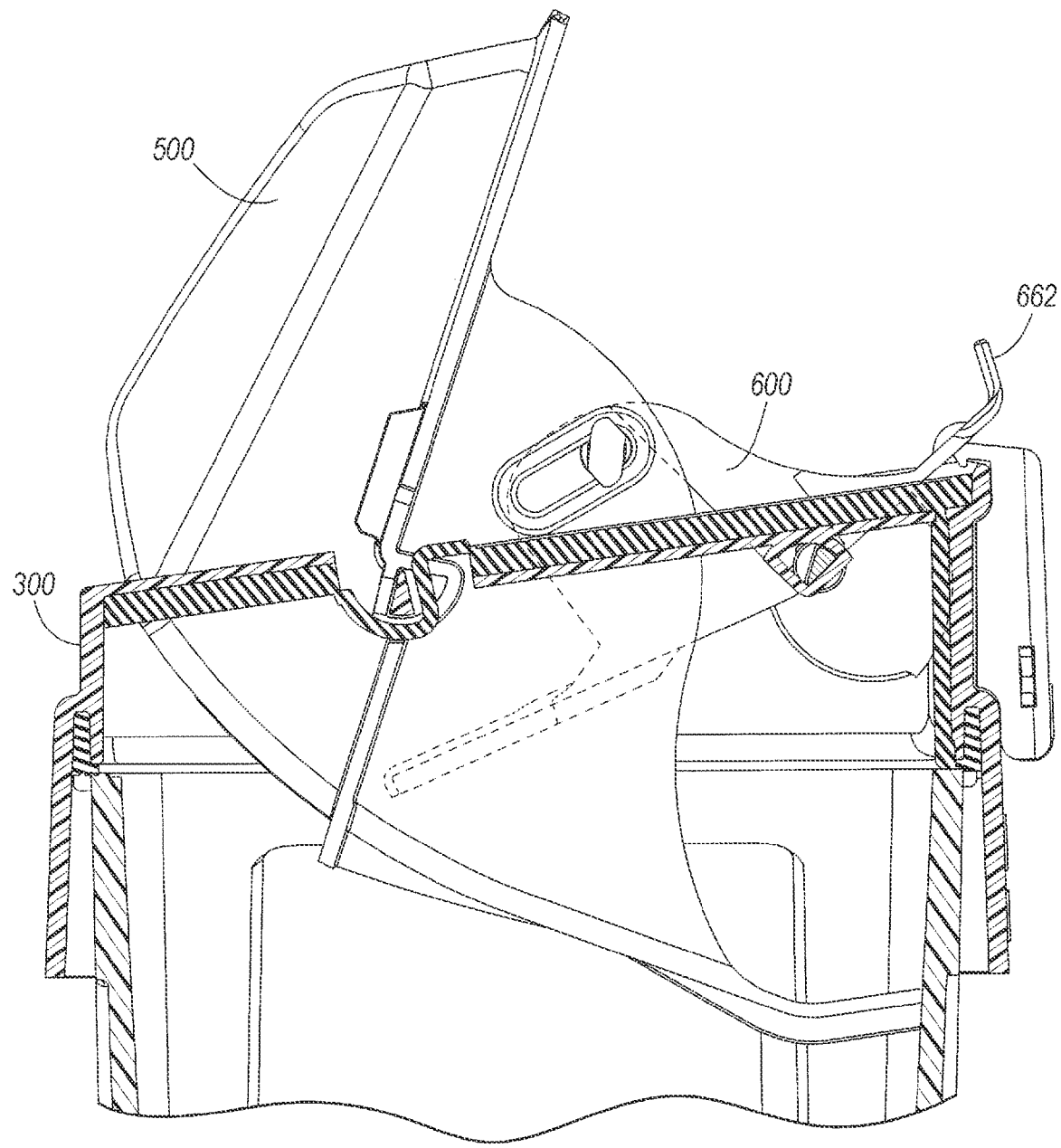
FIG. 7c is a partial section view taken along line 7c-7c of FIG. 7b.
Figure 8A:
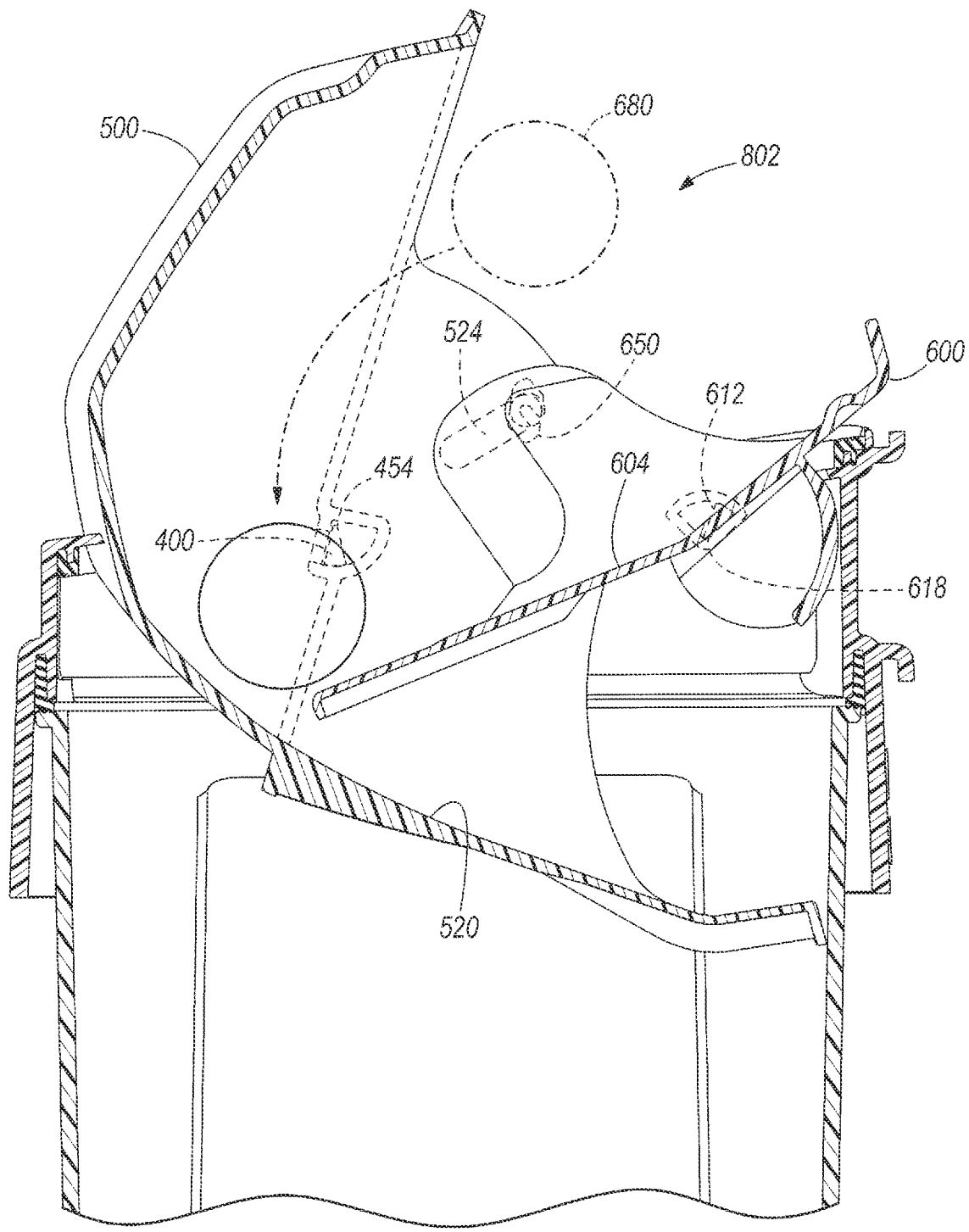
FIG. 8a is a section view showing the operational receiving position of the waste container assembly embodying the present invention.
Figure 8B:
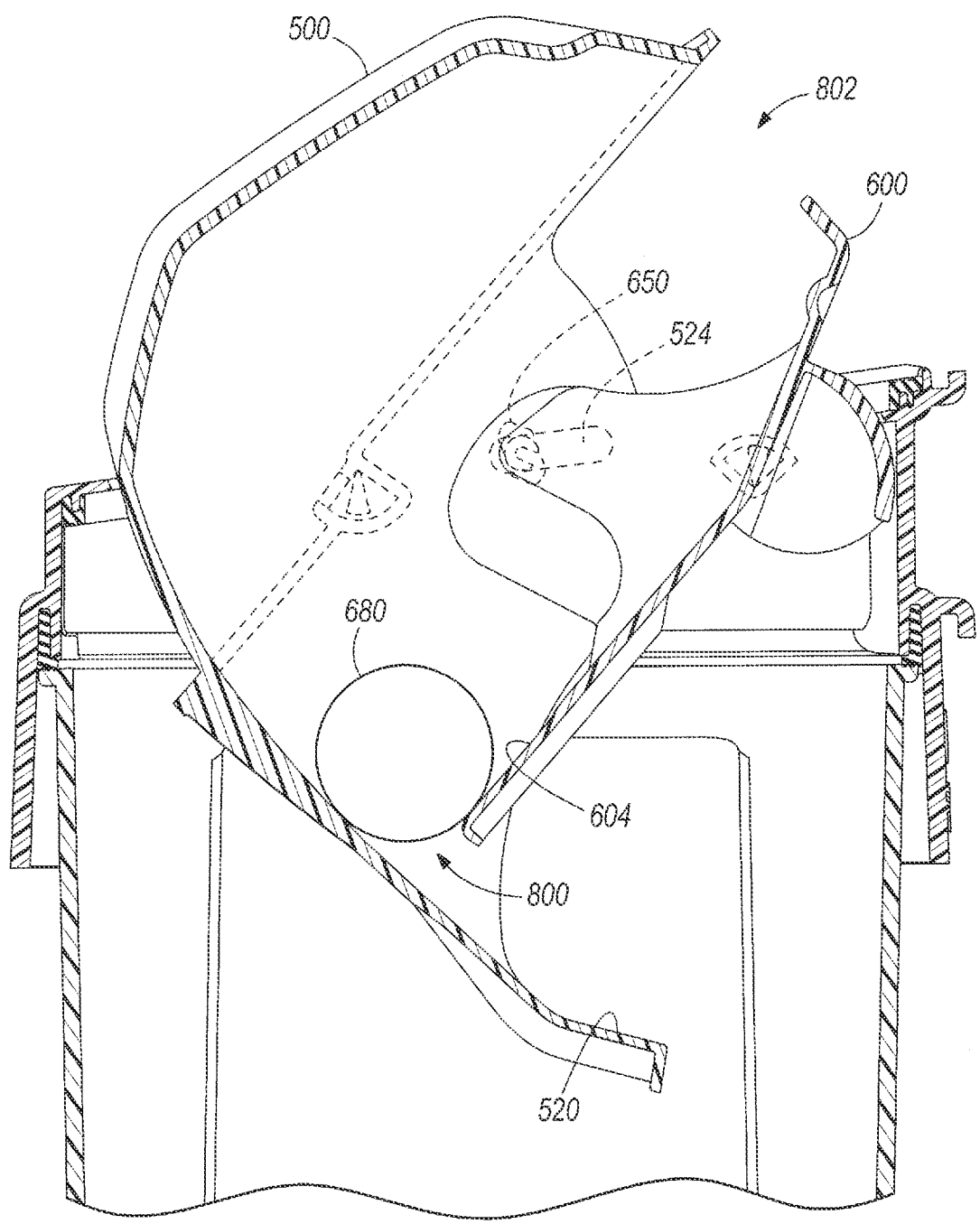
FIG. 8b is a section view showing an operational intermediate position of the waste container assembly between the receiving position of FIG. 8a and an operational disposing position.
Figure 8C:
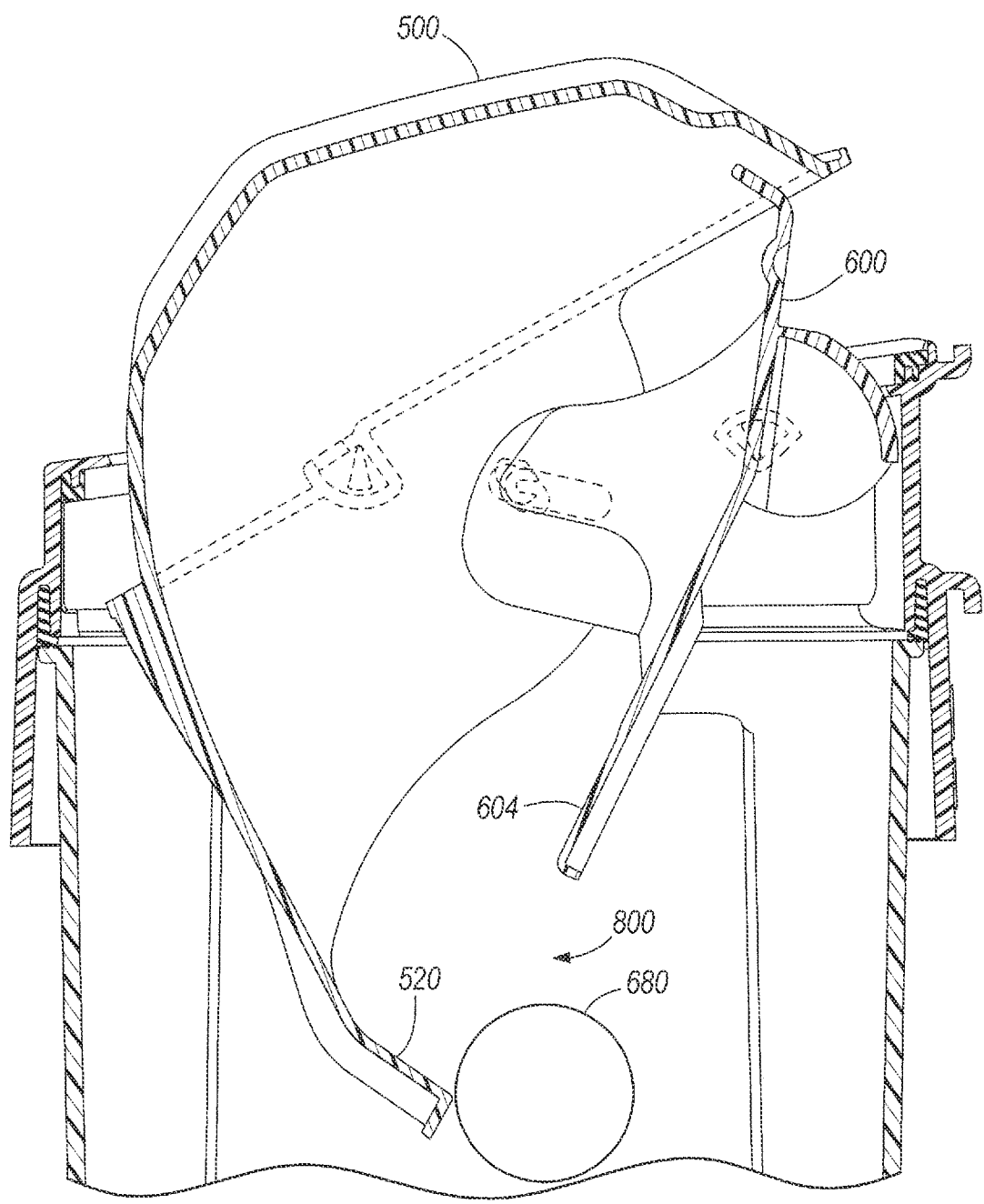
FIG. 8c is a section view showing an operational disposing position of the waste container assembly embodying the present invention.

An underside 624 of the pivoting member 600 includes an arcuate guard 628 that hinders access into the receptacle 100 when the pivoting member 600 is moved toward and into a disposing position (see FIGS. 8b-8c). As shown in FIG. 6c, the opposing side of the arcuate guard 628 includes a series of supporting or reinforcing struts 632. A cavity 636 is formed in the underside 624 to account for interference from the locking latch 700 when the pivot member is in the open or receiving position (see, e.g., FIG. 7c).

Figure 7A:
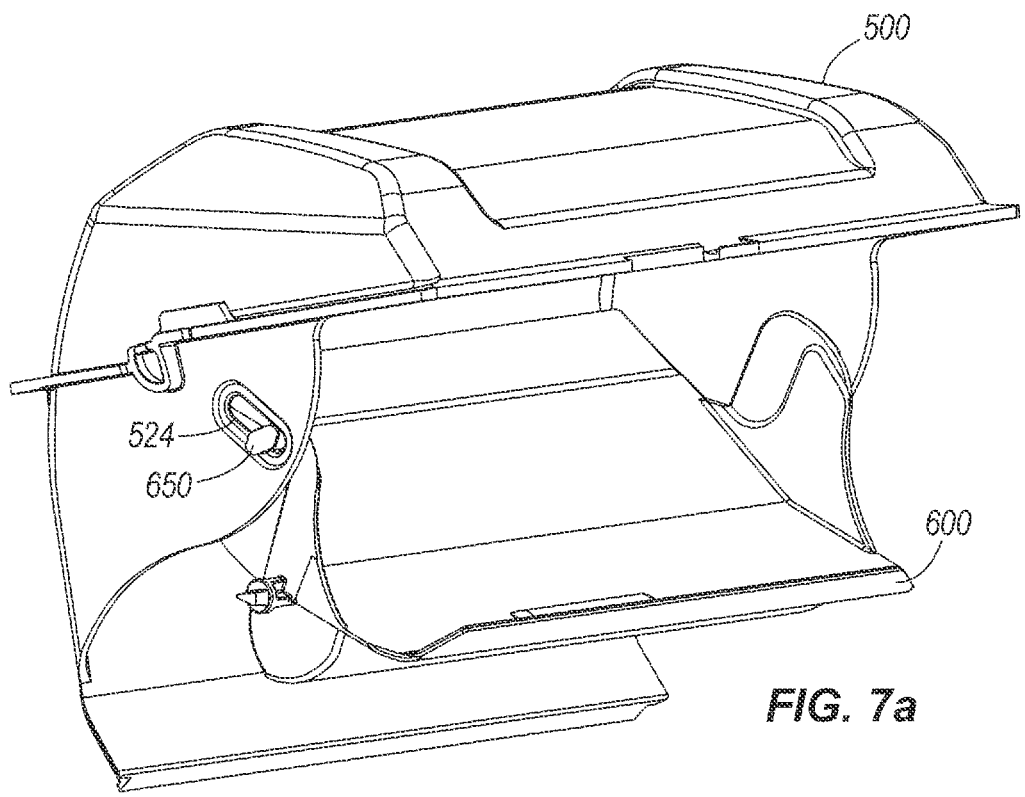
Figure 7B:
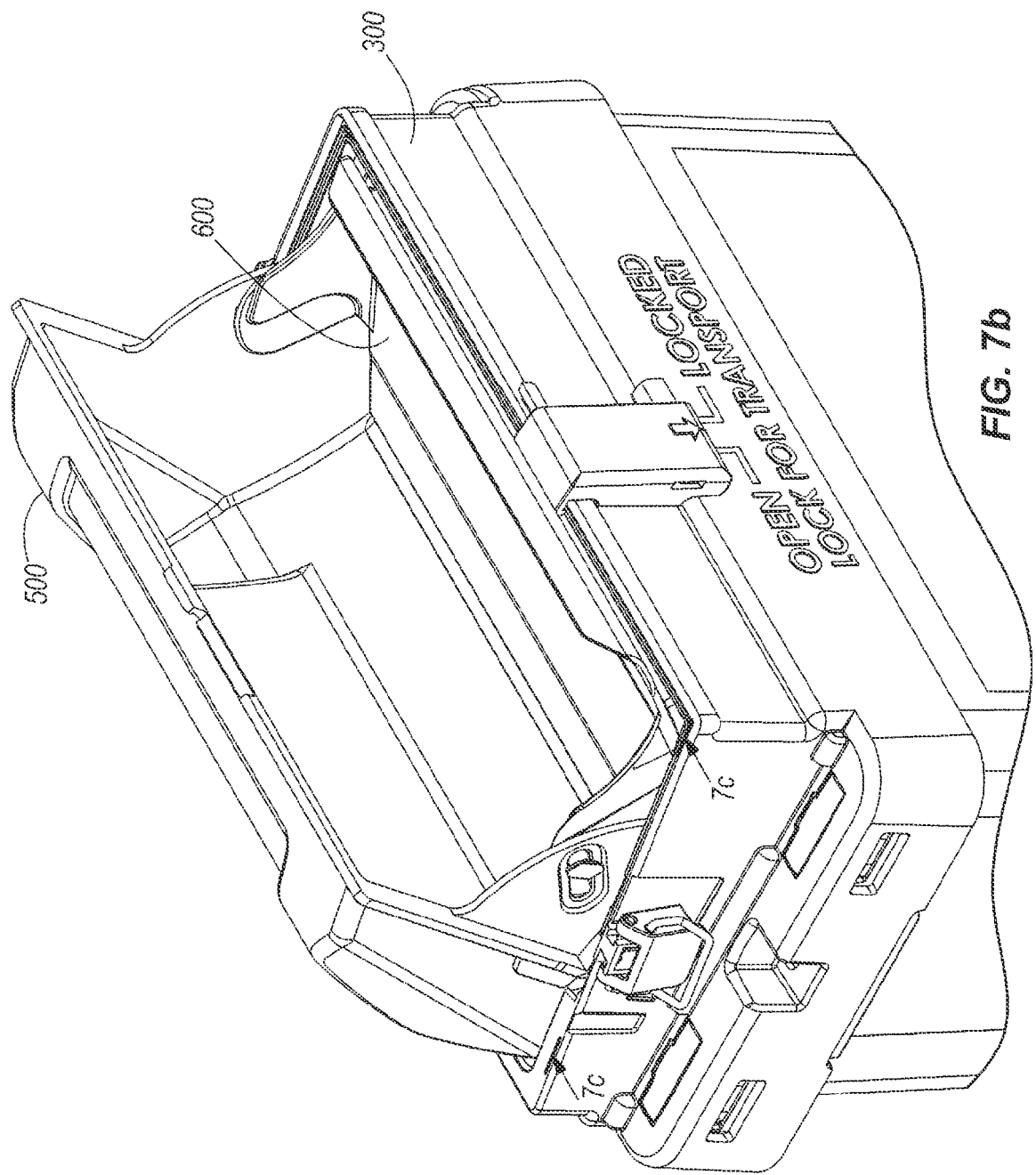

Referring to FIGS. 6a and 6b, a pair of side sections 640 provide a supporting structure for opposing projections 650. The projections 650 each include a shaft 654 for translating within the aperture 524 of the first pivoting member 500 (compare positions of projections 650 within apertures 524 in FIGS. 8a and 8b during concurrent counter rotation of the pivoting member 500, 600) and a stop 658 to limit such movement to translation in two dimensions. As further shown in FIG. 6b, an edge barrier 662 extending from the disposal surface 604 hinders access into the receptacle 100 when the second pivoting member 600 is in a disposing position. For reference, the positioning and operative coupling of pivoting member 500 with respect to pivoting member 600 is shown in FIG. 7a, and the placement and operative coupling of the pivoting members 500, 600 is shown associated with the mounting member 300 in FIGS. 7b and 7c.

In operation, first and second pivoting members 500, 600, are biased to the open or receiving position, as shown in FIG. 8a. The disposal surfaces 520 and 604 together define a tortuous path into the receptacle 100, with the disposal surface 604 inclined downwardly and toward the rear of the mounting member 300, and the disposal surface 520 inclined downwardly and toward the front of the mounting member 300. The disposal surface 604 overlies and partially overlaps the disposal surface 520. A lower terminal end of the disposal surface 520 abuts or nearly abuts the interior surface of the receptacle 100.

Waste 680 is placed on or contacts either of disposal surfaces 520, 604. The weight of the waste initiates rotation of the contacted pivoting member, with the first pivoting member 500 rotating about the pivot surfaces 454 of the pivot projections 440 and the second pivoting member 600 rotating about the pivot surfaces 618 of the pivot projections 612. Due to the cooperation of the previously described opposing apertures 524 of the first pivoting member 500 with the opposing projections 650 of the second pivoting member 600, concurrent counter rotation of pivoting members 500, 600 occurs, as shown in FIG. 8b, wherein at an intermediate position between the receiving position and a disposing position, an opening 800 between the disposal surfaces 520, 604 enlarges to allow the waste 680 to begin to fall through to the receptacle 100. At the same time, an opening 802, through which the waste 680 was initially inserted, gets smaller. Referring to FIG. 8c, a disposing position is reached, which may occur after the waste has fallen into the receptacle 100. The disposing position varies with the size of the waste 680 being disposed and will generally approach, and may briefly coincide with, the closed position (see FIG. 1) with larger pieces of waste 680. The opening 800 is at its greatest at the disposing position. The unbalanced nature of the cooperating pivoting members 500, 600 in the disposing position causes rotation back to the receiving position of FIG. 8a.

Figure 11B:
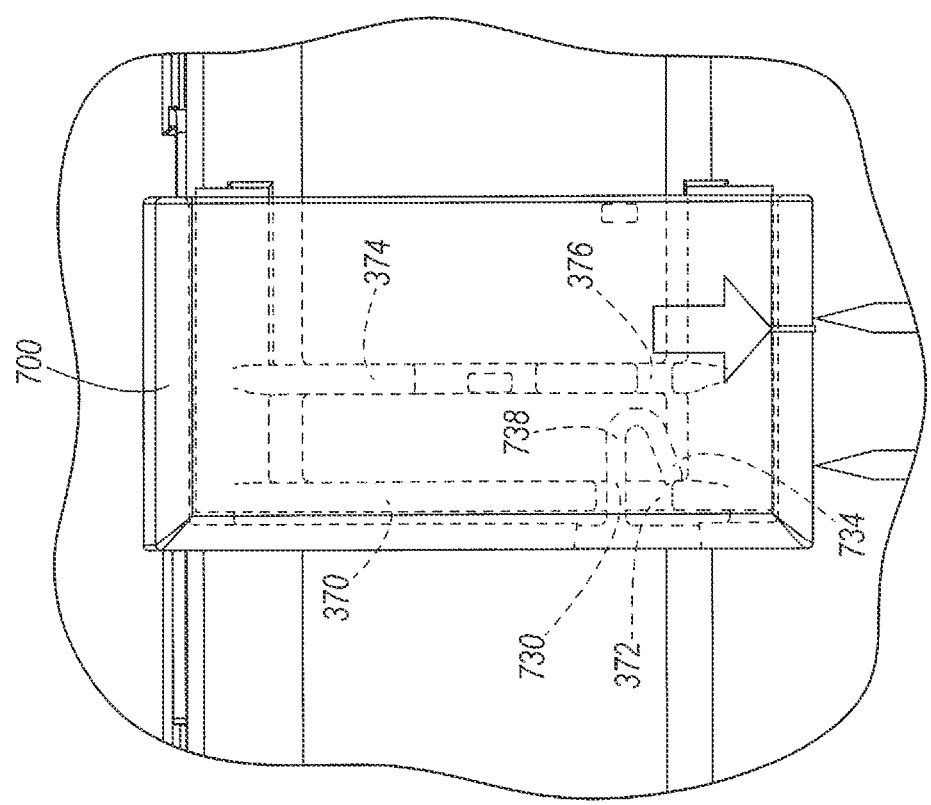
Figure 11A:
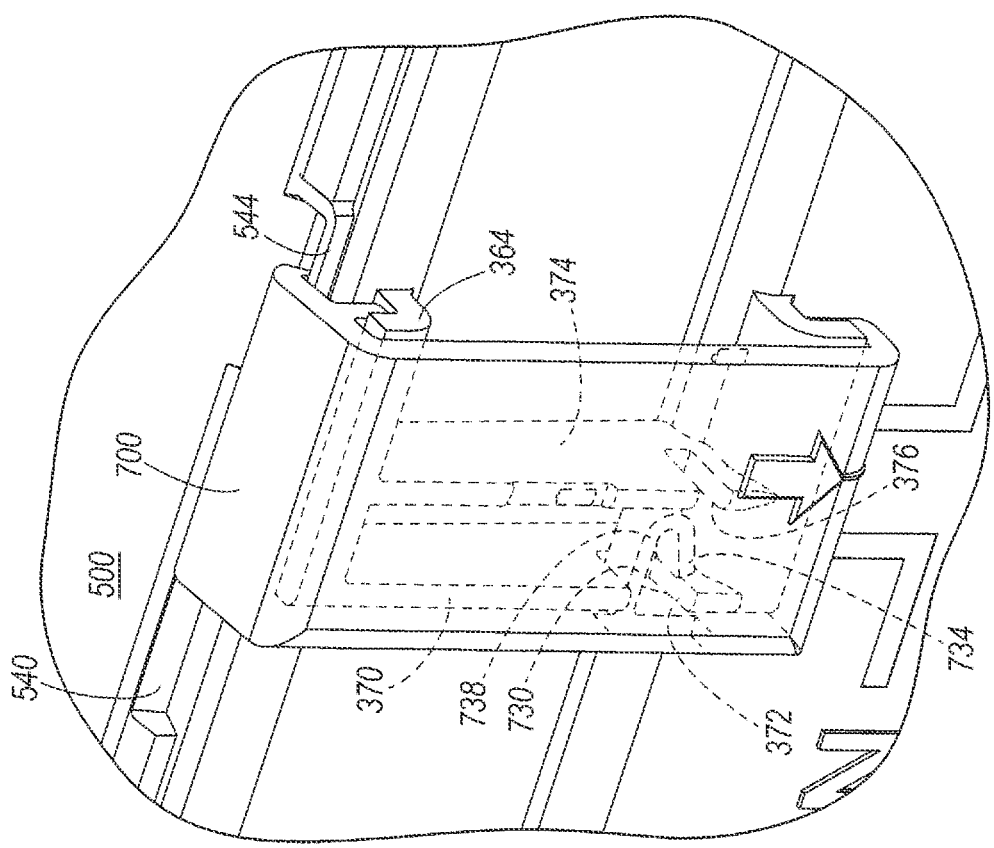
FIG. 11a is a partial perspective view of the locking latch of FIG. 9 in a locked position.

Referring to FIG. 9, the locking latch 700 includes a planar interior surface 704, a lower receiving edge 708, and an upper receiving edge 712. The lower receiving edge 708 receives the lower lip 316 of the front face 312 for securing the locking latch 700 to the mounting member 300. The upper receiving edge 712 includes a first tab 716 for receiving the upper lip 364 of the front face 360. Slidably secured on lower lip 316 and upper lip 364, the locking latch 700 translates from an open position to a locked position on the mounting member 300. As shown in FIGS. 10a and 10b, in the open position, the locking latch 700 is positioned such that a second tab 720 sits within the depression 542 of the first pivoting member 500 when the pivoting member 500 is in a closed position. When the user desires to lock the container assembly 10 for disposal, the user slides the locking latch 700 rightward (in FIGS. 10a and 10b) and over the locking lip 544 to secure the pivoting member 500 to the mounting member 300, as shown in FIGS. 11a and 11b. Referring to FIGS. 9-11b, the locking latch 700 includes a hook 730. During locking, an end 734 of the hook 730 is compressed toward the hook shaft 738 while it passes through the opening 372 of the locking engagement member 370. Once through, the stored energy of compression releases the end 734 of the hook 730 such that the hook 730 prevents the locking latch 700 from returning to the open position, as best illustrated in FIGS. 11a and 11b. Only through use of a specialized tool (not shown) inserted from the rightward direction through the opening 376 of the locking release member 374 to recompress the end 734 of the hook 730 so the locking latch 700 can be moved back to the open position. A detent 750 on the interior surface 704 of the locking latch 700 (FIG. 9) provides resistance to movement against the locking engagement member 370 from the open position to the locked position to hinder inadvertent locking of the locking latch 700. In the presently described embodiment, the closed position of the container assembly 10, as illustrated in FIG. 1, can be maintained using the locking latch 700, the closure latches 580 as previously described, or a combination of the two.

The container assembly 10 and associated components as described can be formed from plastic, and can particularly be injection molded plastic parts. Other materials and methods of manufacture do not limit the container assembly 10 hereinbefore described. In addition, the assembly of the presently described embodiment is not limited in its use to disposal of medical waste, but rather could be used for any disposal application in which hindered access to the disposed items is desired.

Various features and advantages of the invention are set forth in the following claims.

What is claimed is:

1. A container for disposing of waste, the container comprising:
   a receptacle;
   a first pivoting member functionally associated with the receptacle and having a first disposal surface, a hood merging with the first disposal surface, and a pair of opposing sides adjoining the hood with the first disposal surface; and
   a second pivoting member functionally associated with the receptacle and having a second disposal surface, wherein the second pivoting member is operatively coupled to the first pivoting member such that waste deposited on either the first disposal surface or the second disposal surface causes concurrent counter rotation of both the first pivoting member and the second pivoting member to dispose of the waste into the receptacle,
wherein one of the first pivoting member and the second pivoting member includes a pair of opposing projections, and the other of the first pivoting member and the second pivoting member includes a pair of apertures, and wherein the opposing projections translate within the opposing apertures during the concurrent counter rotation, and
wherein a portion of the second pivoting member extends into a space defined between the hood and the pair of opposing sides of the first pivoting member during at least a portion of the counter rotation and the hood is configured to be selectively latched to the receptacle in a closed position.

2. The container of claim 1, wherein the first pivoting member and the second pivoting member cooperate to define a first position in which the first disposal surface and the second disposal surface are configured to receive the waste.

3. The container of claim 2, wherein the first pivoting member and the second pivoting member cooperate to define a second position in which the first disposal surface and the second disposal surface are configured for disposal of the waste into the receptacle.

4. The container of claim 2, wherein the first pivoting member and the second pivoting member are configured to hinder access into the receptacle when in the first position.

5. The container of claim 3, wherein the second pivoting member further includes an arcuate portion configured to hinder access into the receptacle when in the second position.

6. The container of claim 5, wherein the second pivoting member includes an underside surface opposite the first disposal surface, and wherein the arcuate portion is coupled to the underside surface.

7. The container of claim 3, wherein the first pivoting member further includes a hood portion configured to hinder access into the receptacle when in the second position.

8. The container of claim 2, wherein when in the first position, the first disposal surface and the second disposal surface define a tortuous path into the receptacle.

9. The container of claim 1, wherein the opposing apertures are slots.

10. The container of claim 1, further including a mounting member coupled to the receptacle, wherein the first pivoting member and the second pivoting member are pivotally coupled to the mounting member.

11. The container of claim 10, wherein the mounting member and the first pivoting member are pivotally coupled via a pivot projection received in a pivot seat.

12. The container of claim 10, wherein the mounting member and the second pivoting member are pivotally coupled via a pivot projection received in a pivot seat.

13. The container of claim 10, wherein the mounting member and the first pivoting member are pivotally coupled via a pair of pivot projections received in a respective pair of pivot seats, and wherein the mounting member and the second pivoting member are pivotally coupled via a pair of pivot projections received in a respective pair of pivot seats.

14. The container of claim 10, further including a locking latch, wherein the locking latch secures the first pivoting member to the mounting member to prevent access to the receptacle.

15. The container of claim 14, wherein the locking latch is a sliding latch, whereby the sliding latch moves linearly from an open position to a locked position.

16. The container of claim 10, further including at least one closure latch, wherein the at least one closure latch secures the first pivoting member to the mounting member.

17. The container of claim 16, further including a gasket coupled to the mounting member, the closure latch operable to compress the gasket between the first pivoting member and the mounting member for sealing.

18. The container of claim 16, further including a locking latch, wherein the locking latch further secures and locks the first pivoting member to the mounting member to prevent access to the receptacle.

* * * * *